United States Patent
Meyer et al.

(10) Patent No.: US 9,125,936 B2
(45) Date of Patent: Sep. 8, 2015

(54) GINGER EXTRACT FOR THE PROTECTION OF STEM CELLS

(71) Applicant: Symrise AG, Holzminden (DE)

(72) Inventors: Imke Meyer, Bodenwerder (DE); Martina Herrmann, Hameln (DE); Dominik Stuhlmann, Düsseldorf (DE); Holger Joppe, Dassel (DE)

(73) Assignee: Symrise AG, Holzminden (DE)

( * ) Notice: Subject to any disclaimer, the term of this patent is extended or adjusted under 35 U.S.C. 154(b) by 0 days.

(21) Appl. No.: 14/185,157

(22) Filed: Feb. 20, 2014

(65) Prior Publication Data

US 2014/0242020 A1   Aug. 28, 2014

(30) Foreign Application Priority Data

Feb. 27, 2013  (EP) .................... 13156979

(51) Int. Cl.

| | |
|---|---|
| *A61K 36/9068* | (2006.01) |
| *A61K 31/12* | (2006.01) |
| *A61K 8/97* | (2006.01) |
| *A61K 8/35* | (2006.01) |
| *A61Q 19/00* | (2006.01) |
| *A61Q 7/00* | (2006.01) |
| *A61Q 19/08* | (2006.01) |
| *A61Q 5/00* | (2006.01) |
| *A61Q 5/12* | (2006.01) |
| *A61Q 15/00* | (2006.01) |
| *A61Q 19/02* | (2006.01) |
| *A61Q 19/06* | (2006.01) |

(52) U.S. Cl.
CPC .............. *A61K 36/9068* (2013.01); *A61K 8/35* (2013.01); *A61K 8/97* (2013.01); *A61K 31/12* (2013.01); *A61Q 7/00* (2013.01); *A61Q 19/00* (2013.01); *A61K 2236/37* (2013.01); *A61K 2236/39* (2013.01); *A61K 2800/75* (2013.01); *A61Q 5/006* (2013.01); *A61Q 5/12* (2013.01); *A61Q 15/00* (2013.01); *A61Q 19/02* (2013.01); *A61Q 19/06* (2013.01); *A61Q 19/08* (2013.01)

(58) Field of Classification Search
None
See application file for complete search history.

(56) References Cited

U.S. PATENT DOCUMENTS 6,541,046 B2 *  4/2003  Wei et al. ...................... 424/756
2011/0280976 A1   11/2011  Castor

OTHER PUBLICATIONS

Kawai (Planta Med (1994), vol. 60, pp. 17-20).*
http://www.quackwatch.com/01QuackeryRelatedTopics/antiagingpp.html—accessed May 2014.*
Jolad et al: "Fresh organically grown ginger (Zingiber officinale): composition and effects on LPS-induced PGE2 production," Phytochemistry vol. 65, pp. 1937-1954 (2004).
Lee et al: "Protective Effects of Ginger Supercritical Extract against Oxidative Damage in L6 Muscle Cells," J. Korean Soc. Appl. Biol. Chem. 54(5), pp. 790-794 (2011).
Guahk et al: "Zingiber officinale Protects HaCaT cells and C57BL/6 Mice from Ultraviolet B-Induced Inflammation," J. Med. Food 13(3), pp. 673-680 (2010).
Nakatani et al: "Antioxidants in Ginger Family," Quality Management of Nutraceuticals vol. 803, pp. 230-240 (Dec. 17, 2001).
Martinez: "Supercritical Fluid Extraction of Nutraceuticals and Bioactive Compounds," Taylor & Francis Group, LLC, pp. 337-366 (2008).
Yonei et al: "Extraction of Ginger Flavor with Liquid or Supercritical Carbon Dioxide," The Journal of Supercritical Fluids vol. 8, pp. 156-161 (1995).

* cited by examiner

*Primary Examiner* — Susan Hoffman
(74) *Attorney, Agent, or Firm* — Dilworth & Barrese, LLP

(57) ABSTRACT

Ginger extract compositions containing 25 to 30% b.w. [6]-gingerol, 5 to 10% b.w. [8]-gingerol, 5 to 10% b.w. [10]-gingerol, 1.5 to 4% b.w. [6]-shogaol, 0.3 to 1.3% b.w. [8]-shogaol, 0.03 to 1% b.w. [10]-shogaol and 0.01 to 1% b.w. zingerone, with the amount of gingerols totaling 35 to 50% b.w. and the amount of shogaols totaling 1.5 to 6% b.w.

15 Claims, 1 Drawing Sheet

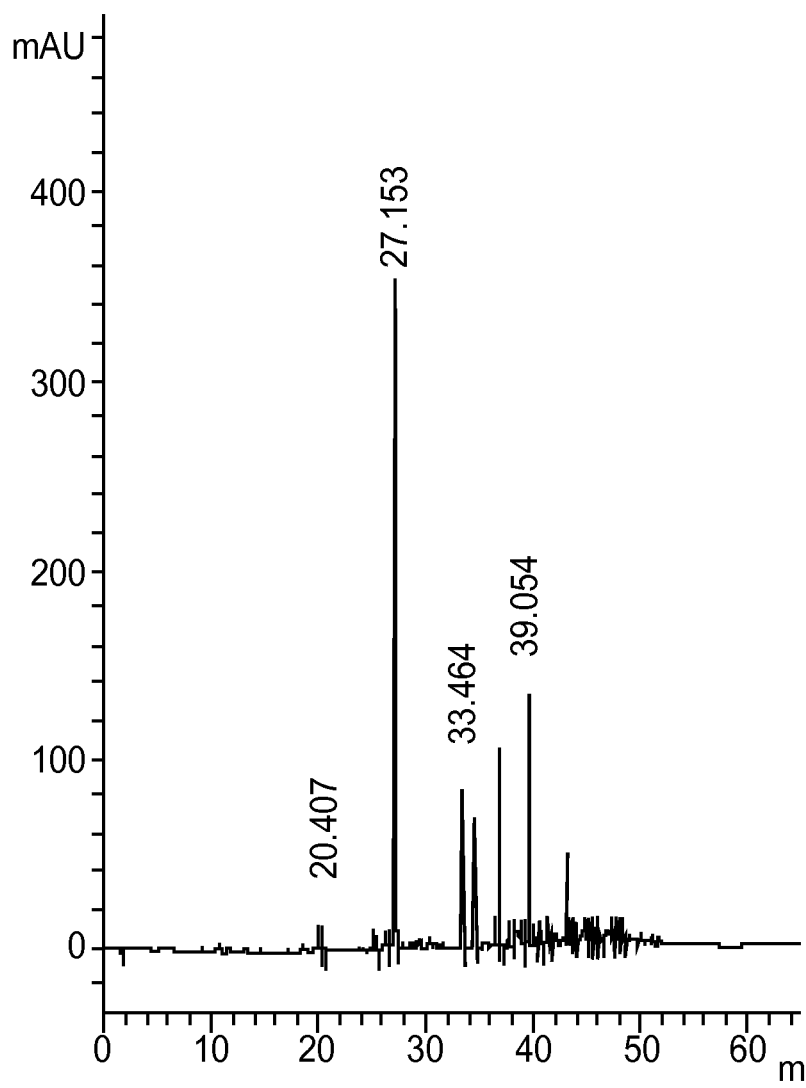

GINGER EXTRACT FOR THE PROTECTION OF STEM CELLS

FIELD OF INVENTION

The present invention belongs to the area of cosmetics and refers to new ginger extracts in particular useful for skin and hair care products.

STATE OF THE ART

The stem cells, which are located near the hair follicles, are responsible for the gradually slowing down of the skin renewal system with aging. As a consequence the skin complexion changes from a luminous shine to a dull appearance, from a smooth to a wrinkled surface, from dense to thin skin (Grove et al., J Gerontol 1983, 38(2):137-42). The hair as an appendage of the skin is also affected by the aging of the stem cells: The hair colour is becoming grey to white, the hair structure is changing to a thin and fragile structure, the hair renewal is decreasing resulting in hair loss and baldness. It took years of research to locate the particular stem cell niches, to identify mechanism leading to a stem cell fade and to develop first ideas to protect the maintenance of these progenitor cells to proliferate and differentiate.

The hair follicle is a mini-organ which hosts four different stem cell populations in overlapping niches to keep a homeostasis in skin and hair integrity (Hodgkinson et al., Expert Rev Med Devices 2009, 6(6): 621-40). To ensure the maintenance of the stem cell populations the microenvironment of these niches is multi-faceted and can change suddenly due to injury but also progressively with cumulative alterations in consequence of UV irradiation and other external stressors (Fuchs, Cell Stem Cell 2009, 4(6): 499-502).

In the hair follicle, epithelial stem cells, in principle multipotent stem cells, are located in the bulge, forming hair follicle, epidermis, sebaceous gland, and apocrine gland (Tiede et al., Eur J Cell Biol 2007, 86(7): 355-76). Directly adherent to the epithelial stem cell population is the melanocyte stem cell population residing in the hair follicle bulge-subbulge area, the lower permanent portion of the hair follicle, to serve as a melanocyte reservoir for skin and hair pigmentation (Nishimura, Pigment Cell Melanoma Res 2011, 24(3): 401-10).

Keeping the stem cells of the skin, especially the stem cells of the bulge and bulge-subbulge area of the hair follicle, in a healthy status guarantees the maintenance of these stem cell populations to proliferate and differentiate and by this the maintenance of the skin and hair renewal system.

The hair follicle undergoes cyclical bouts of regeneration (anagen), degeneration (catagen), and rest (telogen) phase. The epithelial stem cell population in the bulge is synchronized with these phases forming the hair itself and the follicle channel. By the protection of the epithelial stem cell population the homeostasis of the hair follicle is given and aging phenomenons like hair loss, hair thinning, baldness and alopecia are prevented.

Genetic disposition as well as the natural aging process and/or disease contribute to hair loss and slower hair growth in both males and females. Approximately 50% of the population displays this trait to some degree by the age of 50, where thinning of the hair can begin between 12 and 40 years of age independent of gender (Otberg et al., Endocrinol Metab Clin North Am. 2007, 36(2), 379-398 and Price, Investig Dermatol Symp Proc. 2003, 8 (1), 24-27). Studies reveal psychosocial impact with hair loss to include body image dissatisfaction associated with negative stereotypes such as feeling older, weaker and less attractive (Pickard-Holley, Sem. Oncol. Nurs. 1995, 11, 235-238).

Agents which are able to stimulate hair growth by prolonging the phase of production of hair material and/or shortening the resting phase of hair follicles as well as to slow down or reduce hair loss are known as a cure for alopecia. Examples for agents stimulating hair growth by altering the hair follicle cycle are e.g. drugs; including Minoxidil (Rogaine), Finasteride (Propecia) and Dutasteride (Avodart) are approved treatments for hair loss. However, they require medical prescription, and are active only on a certain percentage of the population. Moreover, some of these drugs are not permitted to be used by females because of hormonal effects. Thus, premenopausal women should not take Finesteride due to the risk of abnormalities in male fetus when becoming pregnant (Krus et al., J. Appl. Cosmetol. 2007, 25, 59-74).

Minoxidil is a drug that is effective in inducing hair growth for a small percentage of patients and will re-grow hair only on top of the scalp. Adverse effects when taken orally are tachycardia, angina pectoris and fluid retention. When applied topically adverse effects are mainly dermatologic, i.e. local irritation, itching, dryness and erythema.

Other medical treatments available to treat hair loss include drastic surgical techniques such as scalp reduction, scalp flaps or follicular unit transplantation. These surgeries carry the risk of complications such as elevation of hairline associated with donor region, possibility of necrosis and unnatural appearance of hair growth direction, anesthesia and post-op care, not to mention high costs.

The alteration of the hair follicle cycle helps to retard the hair loss. But to protect from hair loss, hair thinning, baldness and alopecia the protection of the stem cell population is a sustainable mechanism. The onset of hair loss, hair thinning, baldness and alopecia is delayed when the epithelial stem cell population maintains the capacity to proliferate and differentiate, also known as sternness of the stem cells.

An incomplete maintenance of melanocyte stem cells in the bulge-subbulge area was shown to cause physiologic hair greying/canities through the loss of the differentiated progeny with aging (Nishimura et al., Science 2005, 307(5710): 720-4). A disturbed homeostasis of the melanocyte stem cell population is also known to result in pigmentation disorders like vitiligo and leucoderma although the mechanisms are not identified in detail. But it was already shown that the repigmentation of skin affected by the hypopigmentation disorder vitiligo is possible by the transplantation of functional hair follicle melanocyte stem cells (Vanscheidt et al, Dermatology 2009; 218(4): 342-3) to the affected skin.

By keeping stem cells in a healthy status and protect them against intrinsic and extrinsic stress factors, in particular by protecting them against apoptosis, the skin and hair are protected against aging and the hair against loss and greying. Therefore, the object of the present invention has been developing a new active that simultaneously protect stem cells in particular against damaging by UV radiation, and is useful for fighting the ageing of skin and hair, in particular against skin wrinkling, hair-greying, pigment disorders, hair loss and inflammations.

DESCRIPTION OF THE INVENTION

Object of the present invention is a new ginger extract, comprising
(a) 25 to 30% b.w. [6]-gingerol
(b) 5 to 10% b.w. [8]-gingerol
(c) 5 to 10% b.w. [10]-gingerol
(d) 1.5 to 4% b.w. [6]-shogaol (e) 0.3 to 1.3% b.w. [8]-shogaol;
(f) 0.03 to 1 b.w. [10]-shogaol;
(g) 0.001 to 1% b.w. zingerone,
on condition that the amount of gingerols sums up to 35 to 50% b.w. and the amount of shogaols sums up to 1.5 to 6% b.w.

Another object of the present invention is directed to a ginger extract of the aforesaid composition, obtainable in that dried ginger leaves or roots are subjected to solvent extraction or supercritical extraction with carbon dioxide.

In a preferred embodiment the ginger extract shows a total content of pungent components (gingerols+shogaols+zingerones) of about 42 to about 50% b.w., preferably about 43 to 47% b.w. and a content of essential oil of less than about 5% b.w., preferably less than about 2.5% b.w.

Surprisingly the ginger (*Zingiber officinale*) root extract characterized by a high content of pungent components according to the present invention is capable to protect stem cells, more particular stem cells of the hair follicle stem cell niche against UVB irradiation and maintain their activity. The ginger extract according to the present invention is additionally a potent anti-oxidant and a potent anti-irritant agent. Thus, the ginger extract according to the present invention is a protector against aging, pigmentation disorders, hair greying and hair loss and thus an agent capable to support well-aging of skin and hair.

BRIEF DESCRIPTION OF THE DRAWING

The present invention will be described in greater detail with reference to the accompanying drawing in which FIG. 1 illustrates an HPLC chromatogram obtained for a ginger extract according to the present invention (ginger extract 30 mg/10 ml EtOH, detected at 280 nm) with peak at 27.1 min: 6-Gingerol, peak at 33.4 min: 8-Gingerol, peak at 34.5 min: 6-Shogaol, peak at 39.0 min: 10-Gingerol and peak at 43.0 min: 12-Gingerol.

DESCRIPTION OF THE PREFERRED EMBODIMENTS

Ginger Extracts

Ginger root extracts with a high content of pungent components are well-known for the flavouring of food and beverages. The characterization of ginger root extracts by HPLC, GC and other analytical methods is well-described. The quantification of pungent components like gingerols, shogaols and zingerone is good laboratory practice. But ginger extracts characterized by a high content of pungent components of 42-50% b.w. have not been described for cosmetic applications before.

The water and/or ethanol and/or water/ethanol extracts of ginger root of unknown composition are described as anti-oxidants and anti-aging agents and are often disclosed as the preferred extracts for these applications. The use of these extracts is described inter alia in JP 2009 073777 A1 for the improvement of wrinkles, in JP 2000 319189 A1 as elastase inhibitors, by Fujimura et al. (Fragrance Journal (2002), 30(6), 38-42) for wrinkle improvement by inhibition of elastase activity. In JP 2007008847 the claimed extract was prepared with 20% ethanol resulting in the concentration of fructosyl dipeptides as active principles.

For the application to hair and scalp ginger tincture, ginger juice and the above mentioned water and/or ethanol and/or water/ethanol extracts of ginger root are well-known. As activities for these extracts on hair and scalp inter alia enhanced microcirculation is described. For example, CN 102451128 A1 suggests a shampoo claimed to prevent hair loss contains 5% ginger juice. JP 63 091315 A1 describes microcirculation enhancing ginger juice in shampoo formations for hair growth stimulation. EP 1281402 B1 (Kao) refers to a ginger extract substantially free of gingerols for hair growth inhibition.

Ginger oil was used as a soothing, relaxing or warming agent in cosmetic formulations in WO 2009 087578 A1 (Foamix). But the document did not disclose the composition of the ginger oil. The essential oil of ginger is known for a strong pungent smell and taste due to the volatile constituents and is not comparable to the ginger pungent extract according to the present invention.

The isolation of the pungent components of ginger is described in different documents. Ficker et al. (Phytotherapy Research (2003), 17(8), 897-902) evaluated the anti-fungal activity of ginger constituents.

The evaluation of anti-inflammatory activity of pungent components of ginger was given in different documents, inter alia by Lantz et al. (Phytomedicine (2007), 14(2-3), 123-128). Additionally the anti-tumour activity and proliferation inhibitory activity on tumour cells were evaluated by different groups, inter alia by Sang et al. (Journal of Agricultural and Food Chemistry (2009), 57(22), 10645-10650).

In CN 1840162 A1 a ginger root $CO_2$ extract is described without specifying the content of pungent components like gingerols and shogaols. The extract is disclosed as an anti-inflammatory extract. Application examples are tablets, pills and capsules for oral consumption. Examples for topical application on skin are not described.

Extraction

The ginger extract according to the invention is preferably extracted of the dried ginger (*Zingiber officinalis*) root (rhizome). The product is prepared by supercritical fluid extraction with natural carbon dioxide or a solvent mixture of comparable polarity. Due to a fractional supercritical fluid extraction the pungent components of ginger are enriched.

Another object of the present invention refers to a process for obtaining the new ginger extract, wherein
(a) ginger roots are frozen at about −10 to about −25° C.,
(b) the frozen roots are shredded, cut and dried at about 20 to about 50° C. for about 10 to about 30 hours,
(c) the dried roots are subjected to supercritical extraction with carbon dioxide at about 25 to about 90° C. and about 220 to about 370 bar for up to 10 hours; and
(d) the extraction product obtained after about 3 hours is collected while the forerun taken from the first three hours is dismissed.

More particular ginger root is frozen at about −15 to about −20° C. The frozen ginger is shredded and cut. Afterwards the material is dried at about 30 to about 40° C. for about 15 to about 25 hours using a continuous flow dryer. The supercritical fluid extraction is performed with carbon dioxide at about 35 to about 50° C. and about 250 to about 350 bar for up to 10, preferably up to 7 hours. The flow rate is within the range of about 10 to about 20 kg $CO_2$/h*kg raw material. The extract of the first fraction in the first 2 to 3 hours is dominated by essential oil after the de-pressurizing process. The extract of the second fraction taken from 3 up to 7 hours from the starting is the extract according to the present invention after the de-pressurizing process.

Pungent components of ginger extract are in means of the present invention gingerols, shogaols, zingerone, gingerdiols, dehydrogingerdiones and paradols.

The extract is characterized by about 42 to about 50% total pungent compounds mainly gingerols and shogaols with the proviso that extract comprises less than 6% shogaols. The content of zingerone in the ginger extract according to the present invention is lower than 1%.

The advantage of the ginger extract according to the present invention is the low content of essential oil with less than about 5% b.w., more preferable less than about 2.5% b.w. Several components of the essential oil of ginger are known skin sensitizers, by way of example citral, citronellol, eugenol, geraniol, isoeugenol, limonene and linalool. By way of example the skin sensitizers citral, Linalool, Citronellol and d-Limonene are limited due to the production procedure to a concentration of about 0.7% b.w., 0.2% b.w., 0.07% b.w. and 0.3%, b.w. respectively.

Due to the low content of essential oil the ginger extract according to the present invention has no to negligible odour when incorporated in a cosmetic formulation in concentrations sufficient to protect stem cells in the skin.

The ginger extract according to the present invention is a brown clear oily liquid with negligible pungent smell and taste.

By the extraction procedure and the resulting enrichment of pungent components a high content of lipophilic components is combined with a low content of essential oil. By this the ginger extract according to the present invention is beneficial with regard to the potent stem cell protection properties and also with regard to negligible smell and with regard to a low sensitizing potential.

Cosmetic Compositions

Another embodiment of the present invention refers to a cosmetic composition comprising the new ginger extract, containing the extract in an amount of from about 0.01 to about 1, preferably from about 0.1 to about 0.5% b.w.—calculated on the total composition.

The preparations according to the invention may contain abrasives, antiacne agents, agents against ageing of the skin, anticellulitis agents, antidandruff agents, antiinflammatory agents, irritation-preventing agents, irritation-inhibiting agents, antioxidants, astringents, perspiration-inhibiting agents, antiseptic agents, antistatics, binders, buffers, carrier materials, chelating agents, cell stimulants, cleansing agents, care agents, depilatory agents, surface-active substances, deodorizing agents, antiperspirants, softeners, emulsifiers, enzymes, essential oils, fibres, film-forming agents, fixatives, foam-forming agents, foam stabilizers, substances for preventing foaming, foam boosters, gelling agents, gel-forming agents, hair care agents, hair-setting agents, hair-straightening agents, moisture-donating agents, moisturizing substances, moisture-retaining substances, bleaching agents, strengthening agents, stain-removing agents, optically brightening agents, impregnating agents, dirt-repellent agents, friction-reducing agents, lubricants, moisturizing creams, ointments, opacifying agents, plasticizing agents, covering agents, polish, gloss agents, polymers, powders, proteins, re-oiling agents, abrading agents, silicones, skin-soothing agents, skin-cleansing agents, skin care agents, skin-healing agents, skin-lightening agents, skin-protecting agents, skin-softening agents, cooling agents, skin-cooling agents, warming agents, skin-warming agents, stabilizers, UV-absorbing agents, UV filters, detergents, fabric conditioning agents, suspending agents, skin-tanning agents, thickeners, vitamins, oils, waxes, fats, phospholipids, saturated fatty acids, mono- or polyunsaturated fatty acids, α-hydroxy acids, polyhydroxy-fatty acids, liquefiers, dyestuffs, colour-protecting agents, pigments, anticorrosives, aromas, flavouring substances, odoriferous substances, polyols, surfactants, electrolytes, organic solvents or silicone derivatives and the like as additional auxiliaries and additives.

A. Surfactants

Other preferred auxiliaries and additives are anionic and/or amphoteric or zwitterionic surfactants. Typical examples of anionic surfactants are soaps, alkyl benzenesulfonates, alkanesulfonates, olefin sulfonates, alkylether sulfonates, glycerol ether sulfonates, methyl ester sulfonates, sulfofatty acids, alkyl sulfates, fatty alcohol ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids such as, for example, acyl lactylates, acyl tartrates, acyl glutamates and acyl aspartates, alkyl oligoglucoside sulfates, protein fatty acid condensates (particularly wheat-based vegetable products) and alkyl(ether) phosphates. If the anionic surfactants contain polyglycol ether chains, they may have a conventional homolog distribution although they preferably have a narrow-range homolog distribution. Typical examples of amphoteric or zwitterionic surfactants are alkyl-betaines, alkylamidobetaines, aminopropionates, aminoglycinates, imidazolinium betaines and sulfobetaines. The surfactants mentioned are all known compounds. Information on their structure and production can be found in relevant synoptic works, cf. for example J. Falbe (ed.), "Surfactants in Consumer Products", Springer Verlag, Berlin, 1987, pages 54 to 124 or J. Falbe (ed.), "Katalysatoren, Tenside and Mineralöladditive (Catalysts, Surfactants and Mineral Oil Additives)", Thieme Verlag, Stuttgart, 1978, pages 123-217. The percentage content of surfactants in the preparations may be from 0.1 to 10% by weight and is preferably from 0.5 to 5% by weight, based on the preparation.

B. Oil Bodies

Suitable oil bodies, which form constituents of the O/W emulsions, are, for example, Guerbet alcohols based on fatty alcohols having 6 to 18, preferably 8 to 10, carbon atoms, esters of linear $C_6$-$C_{22}$-fatty acids with linear or branched $C_6$-$C_{22}$-fatty alcohols or esters of branched $C_6$-$C_{13}$-carboxylic acids with linear or branched $C_6$-$C_{22}$-fatty alcohols, such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_6$-$C_{22}$-fatty acids with branched alcohols, in particular 2-ethylhexanol, esters of $C_{18}$-$C_{38}$-alkylhydroxy carboxylic acids with linear or branched $C_6$-$C_{22}$-fatty alcohols, in particular Dioctyl Malate, esters of linear and/or branched fatty acids with polyhydric alcohols (such as, for example, propylene glycol, dimerdiol or trimertriol) and/or Guerbet alcohols, triglycerides based on $C_6$-$C_{10}$-fatty acids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, esters of $C_2$-$C_{12}$-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$-$C_{22}$-fatty alcohol carbonates, such as, for example, Dicaprylyl Carbonate (Cetiol® CC), Guerbet carbonates, based on fatty alcohols having 6 to 18, preferably 8 to 10, carbon atoms, esters of benzoic acid with linear and/or branched $C_6$-$C_{22}$-alcohols (e.g. Finsolv® TN), linear or branched, symmetrical or asymmetrical dialkyl ethers having 6 to 22 carbon atoms per alkyl group, such as, for example, dicaprylyl ether (Cetiol® OE), ring-opening products of epoxidized fatty acid esters with polyols, silicone oils (cyclomethicones, silicone methicone grades, etc.) and/or aliphatic or naphthenic hydrocarbons, such as, for example, squalane, squalene or dialkylcyclohexanes.

C. Emulsifiers

Other surfactants may also be added to the preparations as emulsifiers, including for example:

products of the addition of 2 to 30 mol ethylene oxide and/or 0 to 5 mol propylene oxide onto linear $C_{8-22}$ fatty alcohols, onto $C_{12-22}$ fatty acids and onto alkyl phenols containing 8 to 15 carbon atoms in the alkyl group;

$C_{12/18}$ fatty acid monoesters and diesters of addition products of 1 to 30 mol ethylene oxide onto glycerol;

glycerol mono- and diesters and sorbitan mono- and diesters of saturated and unsaturated fatty acids containing 6 to 22 carbon atoms and ethylene oxide addition products thereof;

addition products of 15 to 60 mol ethylene oxide onto castor oil and/or hydrogenated castor oil;

polyol esters and, in particular, polyglycerol esters such as, for example, polyglycerol polyricinoleate, polyglycerol poly-12-hydroxystearate or polyglycerol dimerate isostearate. Mixtures of compounds from several of these classes are also suitable;

addition products of 2 to 15 mol ethylene oxide onto castor oil and/or hydrogenated castor oil;

partial esters based on linear, branched, unsaturated or saturated $C_{6/22}$ fatty acids, ricinoleic acid and 12-hydroxystearic acid and glycerol, polyglycerol, pentaerythritol, -dipentaerythritol, sugar alcohols (for example sorbitol), alkyl glucosides (for example methyl glucoside, butyl glucoside, lauryl glucoside) and polyglucosides (for example cellulose);

mono-, di and trialkyl phosphates and mono-, di- and/or tri-PEG-alkyl phosphates and salts thereof;

wool wax alcohols;

polysiloxane/polyalkyl polyether copolymers and corresponding derivatives;

mixed esters of pentaerythritol, fatty acids, citric acid and fatty alcohol and/or mixed esters of $C_{6-22}$ fatty acids, methyl glucose and polyols, preferably glycerol or polyglycerol, polyalkylene glycols and glycerol carbonate.

The addition products of ethylene oxide and/or propylene oxide onto fatty alcohols, fatty acids, alkylphenols, glycerol mono- and diesters and sorbitan mono- and diesters of fatty acids or onto castor oil are known commercially available products. They are homologue mixtures of which the average degree of alkoxylation corresponds to the ratio between the quantities of ethylene oxide and/or propylene oxide and substrate with which the addition reaction is carried out. $C_{12/18}$ fatty acid monoesters and diesters of addition products of ethylene oxide onto glycerol are known as lipid layer enhancers for cosmetic formulations. The preferred emulsifiers are described in more detail as follows:

(i) Partial glycerides. Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride and technical mixtures thereof which may still contain small quantities of triglyceride from the production process. Addition products of 1 to 30 and preferably 5 to 10 mol ethylene oxide onto the partial glycerides mentioned are also suitable.

(ii) Sorbitan esters. Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical mixtures thereof. Addition products of 1 to 30 and preferably 5 to 10 mol ethylene oxide onto the sorbitan esters mentioned are also suitable.

(iii) Polyglycerol esters. Typical examples of suitable polyglycerol esters are Polyglyceryl-2 Dipolyhydroxystearate (Dehymuls® PGPH), Polyglycerin-3-Diisostearate (Lameform® TGI), Polyglyceryl-4 Isostearate (Isolan® GI 34), Polyglyceryl-3 Oleate, Diisostearoyl Polyglyceryl-3 Diisostearate (Isolan® PDI), Polyglyceryl-3 Methylglucose Distearate (Tego Care® 450), Polyglyceryl-3 Beeswax (Cera Bellina®), Polyglyceryl-4 Caprate (Polyglycerol Caprate T2010/90), Polyglyceryl-3 Cetyl Ether (Chimexane® NL), Polyglyceryl-3 Distearate (Cremophor® GS 32) and Polyglyceryl Polyricinoleate (Admul® WOL 1403), Polyglyceryl Dimerate Isostearate and mixtures thereof. Examples of other suitable polyolesters are the mono-, di- and triesters of trimethylol propane or pentaerythritol with lauric acid, cocofatty acid, tallow fatty acid, palmitic acid, stearic acid, oleic acid, behenic acid and the like optionally reacted with 1 to 30 mol ethylene oxide.

(iv) Anionic emulsifiers. Typical anionic emulsifiers are aliphatic $C_{12-22}$ fatty acids, such as palmitic acid, stearic acid or behenic acid for example, and $C_{12-22}$ dicarboxylic acids, such as azelaic acid or sebacic acid for example.

(v) Amphoteric emulsifiers. Other suitable emulsifiers are amphoteric or zwitterionic surfactants. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocamidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH— or —SO$_3$H— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12/18}$ acyl sarcosine.

D. Superfatting Agents and Consistency Factors

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

The consistency factors mainly used are fatty alcohols or hydroxyfatty alcohols containing 12 to 22 and preferably 16 to 18 carbon atoms and also partial glycerides, fatty acids or hydroxyfatty acids. A combination of these substances with alkyl oligoglucosides and/or fatty acid N-methyl glucamides of the same chain length and/or polyglycerol poly-12-hydroxystearates is preferably used.

E. Thickening Agents and Rheology Additives

Suitable thickeners are polymeric thickeners, such as Aerosil® types (hydrophilic silicas), polysaccharides, more especially xanthan gum, guar-guar, agar-agar, alginates and tyloses, carboxymethyl cellulose and hydroxyethyl cellulose, also relatively high molecular weight polyethylene glycol monoesters and diesters of fatty acids, polyacrylates (for example Carbopols® [Goodrich] or Synthalens® [Sigma]), polyacrylamides, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethoxylates and electrolytes, such as sodium chloride and ammonium chloride.

F. Polymers

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat® L, Grünau), quaternized wheat polypeptides, polyethyleneimine, cationic silicone polymers such as, for example, amodimethicone, copolymers of adipic acid and dimethylaminohydroxypropyl diethylenetriamine (Cartaretine®, Sandoz), copolymers of acrylic acid with dimethyl diallyl ammonium chloride (Merquat® 550, Chemviron), polyaminopolyamides and crosslinked water-soluble polymers thereof, cationic chitin derivatives such as, for example, quaternized chitosan, optionally in microcrystalline distribution, condensation products of dihaloalkyls, for example dibromobutane, with bis-dialkylamines, for example bis-dimethylamino-1,3-propane, cationic guar gum such as, for example, Jaguar® CBS, Jaguar® C-17, Jaguar® C-16 of Celanese, quaternized ammonium salt polymers such as, for example, Mirapol® A-15, Mirapol® AD-1, Mirapol® AZ-1 of Miranol and the various polyquarternium types (for example 6, 7, 32 or 37) which can be found in the market under the tradenames Rheocare® CC or Ultragel® 300.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/acrylate copolymers, octylacrylamide/methyl methacrylate/tert.-butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones.

G. Pearlising Waxes

Suitable pearlising waxes are, for example, alkylene glycol esters, especially ethylene glycol distearate; fatty acid alkanolamides, especially cocofatty acid diethanolamide; partial glycerides, especially stearic acid monoglyceride; esters of polybasic, optionally hydroxy-substituted carboxylic acids with fatty alcohols containing 6 to 22 carbon atoms, especially long-chain esters of tartaric acid; fatty compounds, such as for example fatty alcohols, fatty ketones, fatty aldehydes, fatty ethers and fatty carbonates which contain in all at least 24 carbon atoms, especially laurone and distearylether; fatty acids, such as stearic acid, hydroxystearic acid or behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups and mixtures thereof.

H. Silicones

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. Other suitable silicone compounds are simethicones which are mixtures of dimethicones with an average chain length of 200 to 300 dimethylsiloxane units and hydrogenated silicates. A detailed overview of suitable volatile silicones can be found in Todd et al. in Cosm. Toil. 91, 27 (1976).

I. Waxes and Stabilizers

Besides natural oils used, waxes may also be present in the preparations, more especially natural waxes such as, for example, candelilla wax, carnauba wax, Japan wax, espartograss wax, cork wax, guaruma wax, rice oil wax, sugar cane wax, ouricury wax, montan wax, beeswax, shellac wax, spermaceti, lanolin (wool wax), uropygial fat, ceresine, ozocerite (earth wax), petrolatum, paraffin waxes and microwaxes; chemically modified waxes (hard waxes) such as, for example, montan ester waxes, sasol waxes, hydrogenated jojoba waxes and synthetic waxes such as, for example, polyalkylene waxes and polyethylene glycol waxes.

Metal salts of fatty acids such as, for example, magnesium, aluminium and/or zinc stearate or ricinoleate may be used as stabilizers.

J. Primary Sun Protection Factors

Primary sun protection factors in the context of the invention are, for example, organic substances (light filters) which are liquid or crystalline at room temperature and which are capable of absorbing ultraviolet radiation and of releasing the energy absorbed in the form of longer-wave radiation, for example heat.

The formulations according to the invention advantageously contain at least one UV-A filter and/or at least one UV-B filter and/or a broadband filter and/or at least one inorganic pigment. Formulations according to the invention preferably contain at least one UV-B filter or a broadband filter, more particularly preferably at least one UV-A filter and at least one UV-B filter.

Preferred cosmetic compositions, preferably topical formulations according to the present invention comprise one, two, three or more sun protection factors selected from the group consisting of 4-aminobenzoic acid and derivatives, salicylic acid derivatives, benzophenone derivatives, dibenzoylmethane derivatives, diphenyl acrylates, 3-imidazol-4-yl acrylic acid and esters thereof, benzofuran derivatives, benzylidene malonate derivatives, polymeric UV absorbers containing one or more organosilicon radicals, cinnamic acid derivatives, camphor derivatives, trianilino-s-triazine derivatives, 2-hydroxyphenylbenzotriazole derivatives, phenylbenzimidazole sulfonic acid derivatives and salts thereof, anthranilic acid menthyl esters, benzotriazole derivatives and indole derivatives.

In addition, it is advantageous to combine compounds of formula (I) with active ingredients which penetrate into the skin and protect the skin cells from inside against sunlight-induced damage and reduce the level of cutaneous matrix metalloproteases. Preferred respective ingredients, so called arylhydrocarbon receptor antagonists, are described in WO 2007/128723, incorporated herein by reference. Preferred is 2-benzylidene-5,6-dimethoxy-3,3-dimethylindan-1-one.

The UV filters cited below which can be used within the context of the present invention are preferred but naturally are not limiting.

UV filters which are preferably used are selected from the group consisting of
- p-aminobenzoic acid
- p-aminobenzoic acid ethyl ester (25 mol) ethoxylated (INCI name: PEG-25 PABA)
- p-dimethylaminobenzoic acid-2-ethylhexyl ester
- p-aminobenzoic acid ethyl ester (2 mol) N-propoxylated
- p-aminobenzoic acid glycerol ester
- salicylic acid homomethyl ester (homosalates) (Neo Heliopan® HMS)
- salicylic acid-2-ethylhexyl ester (Neo Heliopan® OS)
- triethanolamine salicylate
- 4-isopropyl benzyl salicylate
- anthranilic acid menthyl ester (Neo Heliopan® MA)
- diisopropyl cinnamic acid ethyl ester
- p-methoxycinnamic acid-2-ethylhexyl ester (Neo Heliopan® AV)
- diisopropyl cinnamic acid methyl ester
- p-methoxycinnamic acid isoamyl ester (Neo Heliopan® E 1000)
- p-methoxycinnamic acid diethanolamine salt
- p-methoxycinnamic acid isopropyl ester
- 2-phenylbenzimidazole sulfonic acid and salts (Neo Heliopan® Hydro)
- 3-(4'-trimethylammonium)benzylidene bornan-2-one methyl sulfate
- beta-imidazole-4(5)-acrylic acid (urocanic acid)
- 3-(4'-sulfo)benzylidene bornan-2-one and salts
- 3-(4'-methyl benzylidene)-D,L-camphor (Neo Heliopan® MBC)
- 3-benzylidene-D,L-camphor
- N-[(2 and 4)-[2-(oxoborn-3-ylidene)methyl]benzyl]acrylamide polymer
- 4,4'-[(6-[4-(1,1-dimethyl)aminocarbonyl)phenylamino]-1,3,5-triazine-2,4-diyl)diimino]-bis-(benzoic acid-2-ethylhexyl ester) (Uvasorb® HEB)
- benzylidene malonate polysiloxane (Parsol® SLX)
- glyceryl ethylhexanoate dimethoxycinnamate
- dipropylene glycol salicylate
- tris(2-ethylhexyl)-4,4',4"-(1,3,5-triazine-2,4,6-triyltriimino)tribenzoate (=2,4,6-trianilino-(p-carbo-2'-ethylhexyl-1'-oxy)-1,3,5-triazine) (Uvinul® T150)

Broadband filters which are preferably combined with one or more compounds of formula (I) in a preparation according to the present invention are selected from the group consisting of
- 2-ethylhexyl-2-cyano-3,3-diphenyl acrylate (Neo Heliopan® 303)
- ethyl-2-cyano-3,3'-diphenyl acrylate
- 2-hydroxy-4-methoxybenzophenone (Neo Heliopan® BB)
- 2-hydroxy-4-methoxybenzophenone-5-sulfonic acid
- dihydroxy-4-methoxybenzophenone
- 2,4-dihydroxybenzophenone
- tetrahydroxybenzophenone
- 2,2'-dihydroxy-4,4'-dimethoxybenzophenone
- 2-hydroxy-4-n-octoxybenzophenone
- 2-hydroxy-4-methoxy-4'-methyl benzophenone
- sodium hydroxymethoxybenzophenone sulfonate
- disodium-2,2'-dihydroxy-4,4'-dimethoxy-5,5'-disulfobenzophenone
- phenol, 2-(2H-benzotriazol-2-yl)-4-methyl-6-(2-methyl-3(1,3,3,3-tetramethyl-1-(trimethylsilyl)oxy)disiloxanyl) propyl) (Mexoryl® XL)
- 2,2'-methylene bis-(6-(2H-benzotriazol-2-yl)-4-1,1,3,3-tetramethyl butyl) phenol) (Tinosorb® M)
- 2,4-bis-[4-(2-ethylhexyloxy)-2-hydroxyphenyl]-1,3,5-triazine
- 2,4-bis-[{(4-(2-ethylhexyloxy)-2-hydroxy}phenyl]-6-(4-methoxyphenyl)-1,3,5-triazine (Tinosorb® S)
- 2,4-bis-[{(4-(3-sulfonato)-2-hydroxypropyloxy)-2-hydroxy}phenyl]-6-(4-methoxyphenyl)-1,3,5-triazine sodium salt
- 2,4-bis-[{(3-(2-propyloxy)-2-hydroxypropyloxy)-2-hydroxy}phenyl]-6-(4-methoxyphenyl)-1,3,5-triazine
- 2,4-bis-[{4-(2-ethylhexyloxy)-2-hydroxy}phenyl]-6-[4-(2-methoxyethyl carbonyl)phenylamino]-1,3,5-triazine
- 2,4-bis-[{4-(3-(2-propyloxy)-2-hydroxypropyloxy)-2-hydroxy}phenyl]-6-[4-(2-ethylcarboxyl)phenylamino]-1,3,5-triazine
- 2,4-bis-[{4-(2-ethylhexyloxy)-2-hydroxy}phenyl]-6-(1-methylpyrrol-2-yl)-1,3,5-triazine
- 2,4-bis-[{4-tris-(trimethylsiloxysilylpropyloxy)-2-hydroxy}phenyl]-6-(4-methoxyphenyl)-1,3,5-triazine
- 2,4-bis-[{4-(2"-methylpropenyloxy)-2-hydroxy}phenyl]-6-(4-methoxyphenyl)-1,3,5-triazine
- 2,4-bis-[{4-(1',1',1',3',5',5',5'-heptamethylsiloxy-2"-methylpropyloxy)-2-hydroxy}phenyl]-6-(4-methoxyphenyl)-1,3,5-triazine UV-A filters filters which are preferably combined with one or more compounds of formula (I) in a preparation according to the present invention are selected from the group consisting of
- 4-isopropyl dibenzoyl methane
- terephthalylidene dibornane sulfonic acid and salts (Mexoryl® SX)
- 4-t-butyl-4'-methoxydibenzoyl methane (avobenzone)/ (Neo Heliopan® 357)

phenylene bis-benzimidazyl tetrasulfonic acid disodium salt (Neo Heliopan® AP)

2,2'-(1,4-phenylene)-bis-(1H-benzimidazole-4,6-disulfonic acid), monosodium salt 2-(4-diethylamino-2-hydroxybenzoyl)benzoic acid hexyl ester (Uvinul® A Plus)

indanylidene compounds in accordance with DE 100 55 940 A1 (=WO 2002 038537 A1)

UV filters which are more preferably combined with one or more compounds of formula (I) in a preparation according to the present invention are selected from the group consisting of p-aminobenzoic acid 3-(4'-trimethylammonium)benzylidene bornan-2-one methyl sulfate salicylic acid homomethyl ester (Neo Heliopan® HMS)

2-hydroxy-4-methoxybenzophenone (Neo Heliopan® BB)

2-phenylbenzimidazole sulfonic acid (Neo Heliopan® Hydro)

terephthalylidene dibornane sulfonic acid and salts (Mexoryl® SX)

4-tert-butyl-4'-methoxydibenzoyl methane (Neo Heliopan® 357)

3-(4'-sulfo)benzylidene bornan-2-one and salts 2-ethylhexyl-2-cyano-3,3-diphenyl acrylate (Neo Heliopan® 303)

N-[(2 and 4)-[2-(oxoborn-3-ylidene)methyl]benzyl]acrylamide polymer p-methoxycinnamic acid-2-ethylhexyl ester (Neo Heliopan® AV)

p-aminobenzoic acid ethyl ester (25 mol) ethoxylated (INCI name: PEG-25 PABA)

p-methoxycinnamic acid isoamyl ester (Neo Heliopan® E1000)

2,4,6-trianilino-(p-carbo-2'-ethylhexyl-1'-oxy)-1,3,5-triazine (Uvinul® T150)

phenol, 2-(2H-benzotriazol-2-yl)-4-methyl-6-(2-methyl-3 (1,3,3,3-tetramethyl-1-(trimethylsilyl)oxy)disiloxanyl) propyl) (Mexoryl® XL)

4,4'-[(6-[4-(1,1-dimethyl)aminocarbonyl)phenylamino]-1,3,5-triazine-2,4-diyl)diimino]-bis-(benzoic acid-2-ethylhexyl ester) (Uvasorb HEB)

3-(4'-methyl benzylidene)-D,L-camphor (Neo Heliopan® MBC)

3-benzylidene camphor salicylic acid-2-ethylhexyl ester (Neo Heliopan® OS)

4-dimethylaminobenzoic acid-2-ethylhexyl ester (Padimate O)

hydroxy-4-methoxybenzophenone-5-sulfonic acid and Na salt 2,2'-methylene bis-(6-(2H-benzotriazol-2-yl)-4-1,1,3,3-tetramethyl butyl)phenol) (Tinosorb® M)

phenylene bis-benzimidazyl tetrasulfonic acid disodium salt (Neo Heliopan® AP)

2,4-bis-[{(4-(2-ethylhexyloxy)-2-hydroxy}phenyl]-6-(4-methoxyphenyl)-1,3,5-triazine (Tinosorb® S)

benzylidene malonate polysiloxane (Parsol® SLX)

menthyl anthranilate (Neo Heliopan® MA)

2-(4-diethylamino-2-hydroxybenzoyl)benzoic acid hexyl ester (Uvinul® A Plus)

indanylidene compounds in accordance with DE 100 55 940 (=WO 02/38537).

Advantageous primary and also secondary sun protection factors are mentioned in WO 2005 123101 A1. Advantageously, these preparations contain at least one UVA filter and/or at least one UVB filter and/or at least one inorganic pigment. The preparations may be present here in various forms such as are conventionally used for sun protection preparations. Thus, they may be in form of a solution, an emulsion of the water-in-oil type (W/O) or of the oil-in-water type (O/W) or a multiple emulsion, for example of the water-in-oil-in-water type (W/O/W), a gel, a hydrodispersion, a solid stick or else an aerosol.

In a further preferred embodiment a formulation according to the invention contains a total amount of sunscreen agents, i.e. in particular UV filters and/or inorganic pigments (UV filtering pigments) so that the formulation according to the invention has a light protection factor of greater than or equal to 2 (preferably greater than or equal to 5). Such formulations according to the invention are particularly suitable for protecting the skin and hair.

K. Secondary Sun Protection Factors

Besides the groups of primary sun protection factors mentioned above, secondary sun protection factors of the antioxidant type may also be used. Secondary sun protection factors of the antioxidant type interrupt the photochemical reaction chain which is initiated when UV rays penetrate into the skin. Typical examples are amino acids (for example glycine, histidine, tyrosine, tryptophane) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example alpha-carotene, beta-carotene, lycopene) and derivatives thereof, chlorogenic acid and derivatives thereof, liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, alpha-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and hepta-thionine sulfoximine) in very small compatible dosages, also (metal) chelators (for example alpha-hydroxy-fatty acids, palmitic acid, phytic acid, lactoferrine), alpha-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example linoleic acid, oleic acid), folic acid and derivatives thereof, ubiquinone and ubiquinol and derivatives thereof, vitamin C and derivatives thereof (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutinic acid and derivatives thereof, glycosyl rutin, ferulic acid, furfurylidene glucitol, carnosine, butyl hydroxytoluene, butyl hydroxyanisole, nordihydroguaiac resin acid, nordihydroguaiaretic acid, trihydroxybutyrophenone, uric acid and derivatives thereof, mannose and derivatives thereof, superoxide dismutase, titanium dioxide (for example dispersions in ethanol), zinc and derivatives thereof (for example ZnO, $ZnSO_4$), selenium and derivatives thereof (for example selenium methionine), stilbenes and derivatives thereof (for example stilbene oxide, trans-stilbene oxide) and derivatives of these active substances suitable for the purposes of the invention (salts, esters, ethers, sugars, nucleotides, nucleosides, peptides and lipids).

Advantageous inorganic secondary light protection pigments are finely dispersed metal oxides and metal salts which are also mentioned in WO 2005 123101 A1. The total quantity of inorganic pigments, in particular hydrophobic inorganic micro-pigments in the finished cosmetic preparation according to the present invention is advantageously from 0.1 to 30% by weight, preferably 0.5 to 10.0% by weight, in each case based on the total weight of the preparation.

Also preferred are particulate UV filters or inorganic pigments, which can optionally be hydrophobed, can be used, such as the oxides of titanium ($TiO_2$), zinc (ZnO), iron ($Fe_2O_3$), zirconium ($ZrO_2$), silicon ($SiO_2$), manganese (e.g. MnO), aluminium ($Al_2O_3$), cerium (e.g. $Ce_2O_3$) and/or mixtures thereof.

L. Actives Modulating Skin and/or Hair Pigmentation

Preferred active ingredients for skin and/or hair lightening are selected from the group consisting of:
kojic acid (5-hydroxy-2-hydroxymethyl-4-pyranone), kojic acid derivatives, preferably kojic acid dipalmitate, arbutin, ascorbic acid, ascorbic acid derivatives, preferably magnesium ascorbyl phosphate, hydroquinone, hydroquinone derivatives, resorcinol, resorcinol derivatives, preferably 4-alkylresorcinols and 4-(1-phenylethyl)1,3-dihydroxybenzene (phenylethyl resorcinol), cyclohexylcarbamates (preferably one or more cyclohexyl carbamates disclosed in WO 2010/122178 and WO 2010/097480), sulfur-containing molecules, preferably glutathione or cysteine, alpha-hydroxy acids (preferably citric acid, lactic acid, malic acid), salts and esters thereof, N-acetyl tyrosine and derivatives, undecenoyl phenylalanine, gluconic acid, chromone derivatives, preferably aloesin, flavonoids, 1-aminoethyl phosphinic acid, thiourea derivatives, ellagic acid, nicotinamide (niacinamide), zinc salts, preferably zinc chloride or zinc gluconate, thujaplicin and derivatives, triterpenes, preferably maslinic acid, sterols, preferably ergosterol, benzofuranones, preferably senkyunolide, vinyl guiacol, ethyl guiacol, dionic acids, preferably octodecene dionic acid and/or azelaic acid, inhibitors of nitrogen oxide synthesis, preferably L-nitroarginine and derivatives thereof, 2,7-dinitroindazole or thiocitrulline, metal chelators (preferably alpha-hydroxy fatty acids, phytic acid, humic acid, bile acid, bile extracts, EDTA, EGTA and derivatives thereof), retinoids, soy milk and extract, serine protease inhibitors or lipoic acid or other synthetic or natural active ingredients for skin and hair lightening, the latter preferably used in the form of an extract from plants, preferably bearberry extract, rice extract, papaya extract, turmeric extract, mulberry extract, bengkoang extract, nutgrass extract, liquorice root extract or constituents concentrated or isolated therefrom, preferably glabridin or licochalcone A, *artocarpus* extract, extract of *rumex* and *ramulus* species, extracts of pine species (*pinus*), extracts of *vitis* species or stilbene derivatives isolated or concentrated therefrom, saxifrage extract, *scutelleria* extract, grape extract and/or microalgae extract, in particular *Tetraselmis suecica* Extract.

Preferred skin lighteners as component (b) are kojic acid and phenylethyl resorcinol as tyrosinase inhibitors, beta- and alpha-arbutin, hydroquinone, nicotinamide, dioic acid, Mg ascorbyl phosphate and vitamin C and its derivatives, mulberry extract, Bengkoang extract, papaya extract, turmeric extract, nutgrass extract, licorice extract (containing glycyrrhizin), alpha-hydroxy-acids, 4-alkylresorcinols, 4-hydroxyanisole. These skin lighteners are preferred due to their very good activity, in particular in combination with sclareolide according to the present invention. In addition, said preferred skin lighteners are readily available.

Advantageous skin and hair tanning active ingredients in this respect are substrates or substrate analogues of tyrosinase such as L-tyrosine, N-acetyl tyrosine, L-DOPA or L-dihydroxyphenylalanine, xanthine alkaloids such as caffeine, theobromine and theophyl-line and derivatives thereof, proopiomelanocortin peptides such as ACTH, alpha-MSH, peptide analogues thereof and other substances which bind to the melanocortin receptor, peptides such as Val-Gly-Val-Ala-Pro-Gly, Lys-Ile-Gly-Arg-Lys or Leu-Ile-Gly-Lys, purines, pyrimidines, folic acid, copper salts such as copper gluconate, chloride or pyrrolidonate, 1,3,4-oxadiazole-2-thiols such as 5-pyrazin-2-yl-1,3,4-oxadiazole-2-thiol, curcumin, zinc diglycinate ($Zn(Gly)_2$), manganese(II) bicarbonate complexes ("pseudocat-alases") as described for example in EP 0 584 178, tetrasubstituted cyclohexene derivatives as described for example in WO 2005/032501, isoprenoids as described in WO 2005/102252 and in WO 2006/010661, melanin derivatives such as Melasyn-100 and MelanZe, diacyl glycerols, aliphatic or cyclic diols, psoralens, prostaglandins and analogues thereof, activators of adenylate cyclase and compounds which activate the transfer of melanosomes to keratinocytes such as serine proteases or agonists of the PAR-2 receptor, extracts of plants and plant parts of the *chrysanthemum* species, *san-guisorba* species, walnut extracts, urucum extracts, rhubarb extracts, microalgae extracts, in particular *Isochrysis galbana*, trehalose, erythru-lose and dihydroxyacetone. Flavonoids which bring about skin and hair tinting or browning (e.g. quercetin, rhamnetin, kaempferol, fisetin, genistein, daidzein, chrysin and api-genin, epicatechin, diosmin and diosmetin, morin, quercitrin, naringenin, hesperidin, phloridzin and phloretin) can also be used.

The amount of the aforementioned examples of additional active ingredients for the modulation of skin and hair pigmentation (one or more compounds) in the products according to the invention is then preferably 0.00001 to 30 wt. %, preferably 0.0001 to 20 wt. %, particularly preferably 0.001 to 5 wt. %, based on the total weight of the prepa-ration.

M. Anti-Ageing Actives

In the context of the invention, anti-ageing or biogenic agents are, for example antioxidants, matrix-metalloproteinase inhibitrors (MMPI), skin moisturizing agents, glycosaminglycan stimulkators, anti-inflammatory agents, TRPV1 antagonists and plant extracts.

(i) Antioxidants. amino acids (preferably glycine, histidine, tyrosine, tryptophane) and derivatives thereof, imidazoles (preferably urocanic acid) and derivatives thereof, peptides, preferably D,L-carnosine, D-carnosine, L-carnosine and derivatives thereof (preferably anserine), carnitine, creatine, matrikine peptides (preferably lysyl-threonyl-threonyl-lysyl-serine) and palmitoylated pentapeptides, carotenoids, carotenes (preferably alpha-carotene, beta-carotene, lycopene) and derivatives thereof, lipoic acid and derivatives thereof (preferably dihydrolipoic acid), aurothioglucose, propyl thiouracil and other thiols (preferably thioredoxine, glutathione, cysteine, cystine, cystamine and glycosyl, N-acetyl, methyl, ethyl, propyl, amyl, butyl and lauryl, palmitoyl, oleyl, gamma-linoleyl, cholesteryl, glyceryl and oligoglyceryl esters thereof) and salts thereof, dilauryl thiodipropionate, distearyl thiodipropionate, thiodipropionic acid and derivatives thereof (preferably esters, ethers, peptides, lipids, nucleotides, nucleosides and salts) and sulfoximine compounds (preferably buthionine sulfoximines, homocysteine sulfoximine, buthionine sulfones, penta-, hexa-, heptathionine sulfoximine) in very small tolerated doses (e.g. pmol to μmol/kg), also (metal) chelators (preferably alpha-hydroxy fatty acids, palmitic acid, phytic acid, lactoferrin, alpha-hydroxy acids (preferably citric acid, lactic acid, malic acid), humic acid, bile acid, bile extracts, tannins, bilirubin, biliverdin, EDTA, EGTA and derivatives thereof), unsaturated fatty acids and derivatives thereof (preferably gamma-linolenic acid, linoleic acid, oleic acid), folic acid and derivatives thereof, ubiquinone and derivatives thereof, ubiquinol and derivatives thereof, vitamin C and derivatives (preferably ascorbyl palmitate, Mg ascorbyl phosphate, ascorbyl acetate, ascorbyl glucoside), tocopherols and derivatives (preferably vitamin E acetate), vitamin A and derivatives (vitamin A palmitate) and coniferyl benzoate of benzoic resin, rutinic acid and derivatives thereof, flavonoids and glycosylated precursors thereof, in particular quercetin and derivatives thereof, preferably alpha-glucosyl rutin, rosmarinic acid, carnosol, carnosolic acid, resveratrol, caffeic acid and derivatives thereof, sinapic acid and derivatives thereof, ferulic acid and derivatives thereof, curcuminoids, chlorogenic acid and derivatives thereof, retinoids, preferably retinyl palmitate, retinol or tretinoin, ursolic acid, levulinic acid, butyl hydroxytoluene, butyl hydroxyanisole, nordihydroguaiac acid, nordihydroguaiaretic acid, trihydroxybutyrophenone, uric acid and derivatives thereof, mannose and derivatives thereof, zinc and derivatives thereof (preferably ZnO, $ZnSO_4$), selenium and derivatives thereof (preferably selenium methionine), superoxide dismutase, stilbenes and derivatives thereof (preferably stilbene oxide, trans-stilbene oxide) and the derivatives (salts, esters, ethers, sugars, nucleotides, nucleosides, peptides and lipids) of these cited active ingredients which are suitable according to the invention or extracts or fractions of plants having an antioxidant effect, preferably green tea, rooibos, honeybush, grape, rosemary, sage, *melissa*, thyme, lavender, olive, oats, cocoa, *ginkgo*, ginseng, liquorice, honeysuckle, *sophora, pueraria, pinus*, citrus, *Phyllanthus emblica* or St. John's wort, grape seeds, wheat germ, *Phyllanthus emblica*, coenzymes, preferably coenzyme Q10, plastoquinone and menaquinone. Preferred antioxidants are selected from the group consisting of vitamin A and derivatives, vitamin C and derivatives, tocopherol and derivatives, preferably tocopheryl acetate, and ubiquinone.
(ii) Matrix-Metalloproteinase inhibitors (MMPI). Preferred compositions comprise matrix-metalloproteinase inhibitors, especially those inhibiting matrix-metalloproteinases enzymatically cleaving collagen, selected from the group consisting of: ursolic acid, retinyl palmitate, propyl gallate, precocenes, 6-hydroxy-7-methoxy-2,2-dimethyl-1(2H)-benzopyran, 3,4-dihydro-6-hydroxy-7-methoxy-2,2-dimethyl-1(2H)-benzopyran, benzamidine hydrochloride, the cysteine proteinase inhibitors N-ethylmalemide and epsilon-amino-n-caproic acid of the serinprotease inhibitors: phenylmethylsulfonylfluoride, collhibin (company Pentapharm; INCI: hydrolysed rice protein), oenotherol (company Soliance; INCI: propylene glycol, aqua, *Oenothera biennis* root extract, ellagic acid and ellagitannins, for example from pomegranate), phosphoramidone hinokitiol, EDTA, galardin, EquiStat (company Collaborative Group; apple fruit extract, soya seed extract, ursolic acid, soya isoflavones and soya proteins), sage extracts, MDI (company Atrium; INCI: glycosaminoglycans), fermiskin (company Silab/Mawi; INCI: water and *lentinus edodes* extract), actimp 1.9.3 (company Expanscience/Rahn; INCI: hydrolysed lupine protein), lipobelle soyaglycone (company Mibelle; INCI: alcohol, polysorbate 80, lecithin and soy isoflavones), extracts from green and black tea and further plant extracts, which are listed in WO 02 069992 A1 (see tables 1-12 there, incorporated herein by reference), proteins or glycoproteins from soya, hydrolysed proteins from rice, pea or lupine, plant extracts which inhibit MMPs, preferably extracts from shitake mushrooms, extracts from the leaves of the Rosaceae family, sub-family Rosoideae, quite particularly extracts of blackberry leaf (preferably as described in WO 2005 123101 A1, incorporated herein by reference) as e.g. SymMatrix (company Symrise, INCI: Maltodextrin, *Rubus Fruticosus* (Blackberry) Leaf Extract). Preferred actives of are selected from the group consisting of retinyl palmitate, ursolic acid, extracts from the leaves of the Rosaceae family, sub-family Rosoideae, genistein and daidzein.
(III) Skin-moisturizing agents. Preferred skin moisturizing agents are selected from the group consisting of alkane diols or alkane triols comprising 3 to 12 carbon atoms, preferably $C_3$-$C_{10}$-alkane diols and $C_3$-$C_{10}$-alkane triols. More preferably the skin moisturizing agents are selected from the group consisting of: glycerol, 1,2-propylene glycol, 1,2-butylene glycol, 1,3-butylene glycol, 1,2-pentanediol, 1,2-hexanediol, 1,2-octanediol and 1,2-decanediol.
(iv) Glycosaminoglycan stimulators. Preferred compositions comprise substances stimulating the synthesis of glycosaminoglycans selected from the group consisting of hyaluronic acid and derivatives or salts, Subliskin (Sederma, INCI: *Sinorhizobium Meliloti* Ferment Filtrate, Cetyl Hydroxyethylcellulose, Lecithin), Hyalufix (BASF, INCI: Water, Butylene Glycol, *Alpinia galanga* leaf extract, Xanthan Gum, Caprylic/Capric Triglyceride), Stimulhyal (Soliance, INCI: Calcium ketogluconate), SynGlycan (DSM, INCI: Tetradecyl Aminobutyroylvalylaminobutyric Urea Trifluoroacetate, Glycerin, Magnesium chloride), Kalpariane (Biotech Marine), DC Upregulex (Distinctive Cosmetic Ingredients, INCI: Water, Butylene Glycol, Phospholipids, Hydrolyzed Sericin), glucosamine, N-acetyl glucosamine, retinoids, preferably retinol and vitamin A, *Arctium lappa* fruit extract, *Eriobotrya japonica* extract, Genkwanin, N-Methyl-L-serine, (−)-alpha-bisabolol or synthetic alpha-bisabolol such as e.g. Dragosantol and Dragosantol 100 from Symrise, oat glucan, *Echinacea purpurea* extract and soy protein hydrolysate. Preferred actives are selected from the group consisting of hyaluronic acid and derivatives or salts, retinol and derivatives, (−)-alpha-bisabolol or synthetic alpha-bisabolol such as e.g. Dragosantol and Dragosantol 100 from Symrise, oat glucan, *Echinacea purpurea* extract, *Sinorhizobium Meliloti* Ferment Filtrate, Calcium ketogluconate, *Alpinia galanga* leaf extract and tetradecyl aminobutyroylvalylaminobutyric urea trifluoroacetate.
(v) Anti-inflammatory agents. The compositions may also contain anti-inflammatory and/or redness and/or itch ameliorating ingredients, in particular steroidal substances of the corticosteroid type selected from the group consisting of hydrocortisone, dexamethasone, dexamethasone phosphate, methyl prednisolone or cortisone, are advantageously used as anti-inflammatory active ingredients or active ingredients to relieve reddening and itching, the list of which can be extended by the addition of other steroidal anti-inflammatories. Non-steroidal anti-inflammatories can also be used. Examples which can be cited here are oxicams such as piroxicam or tenoxicam; salicylates such as aspirin, disalcid, solprin or fendosal; acetic acid derivatives such as diclofenac, fenclofenac, indomethacin, sulindac, tolmetin or clindanac; fenamates such as mefenamic, meclofenamic, flufenamic or niflumic; propionic acid derivatives such as ibuprofen, naproxen, benoxaprofen or pyrazoles such as phenylbutazone, oxyphenylbutazone, febrazone or azapropazone. Anthranilic acid derivatives, in particular avenanthramides described in WO 2004 047833 A1, are preferred anti-itch ingredients in a composition according to the present invention.

Also useful are natural or naturally occurring anti-inflammatory mixtures of substances or mixtures of substances that alleviate reddening and/or itching, in particular extracts or fractions from camomile, *Aloe vera, Commiphora* species, *Rubia* species, willow, willow-herb, oats, *calendula, arnica*, St John's wort, honeysuckle, rosemary, *Passiflora incarnata*, witch hazel, ginger or *Echinacea*; preferably selected from the group consisting of extracts or fractions from camomile, *Aloe vera*, oats, *calendula, arnica*, honeysuckle, rosemary, witch hazel, ginger or *Echinacea*, and/or pure substances, preferably alpha-bisabolol, apigenin, apigenin-7-glucoside, gingerols, shogaols, gingerdiols, dehydrogingerdiones, paradols, natural or naturally occurring avenanthramides, preferably tranilast, avenanthramide A, avenanthramide B, avenanthramide C, non-natural or non-naturally occurring avenanthramides, preferably dihydroavenanthramide D, dihydroavenanthramide E, avenanthramide D, avenanthramide E, avenanthramide F, boswellic acid, phytosterols, glycyrrhizin, glabridin and licochalcone A; preferably selected from the group consisting of alpha-bisabolol, natural avenanthramides, non-natural avenanthramides, preferably dihydroavenanthramide D (as described in WO 2004 047833 A1), boswellic acid, phytosterols, glycyrrhizin, and licochalcone A, and/or allantoin, panthenol, lanolin, (pseudo-)ceramides [preferably Ceramide 2, hydroxypropyl bis-palmitamide MEA, cetyloxypropyl glyceryl methoxypropyl myristamide, N-(1-hexadecanoyl)-4-hydroxy-L-proline (1-hexadecyl) ester, hydroxyethyl palmityl oxyhydroxypropyl palmitamide], glycosphingolipids, phytosterols, chitosan, mannose, lactose and β-glucans, in particular 1,3-1,4-β-glucan from oats.

(vi) TRPV1 antagonists. Suitable compounds which reduce the hypersensitivity of skin nerves based on their action as TRPV1 antagonists, encompass e.g. trans-4-tert-butyl cyclohexanol as described in WO 2009 087242 A1, or indirect modulators of TRPV1 by an activation of the μ-receptor, e.g. acetyl tetrapeptide-15, are preferred.

(vii) Botanical extracts. The compositions may also contain various extracts of plants, such as for example extracts of *Ginkgo biloba, Oleacea europensis, Glyzyrrhiza glabra, Vaccinium myrtillus, Trifolium pratense, Litchi sinensis, Vitis, vinifera, Brassica oleracea, Punica granatum, Petroselinium crispum, Centella asiatica, Passiflora incarnata, Medicago sativa, Melissa officinalis, Valeriana officinalis, Castanea sativa, Salix alba* and *Hapagophytum procumbens*.

N. Cooling Agents

The compositions may also contain one or more substances with a physiological cooling effect (cooling agents), which are preferably selected here from the following list: menthol and menthol derivatives (for example L-menthol, D-menthol, racemic menthol, isomenthol, neoisomenthol, neomenthol) menthylethers (for example (I-menthoxy)-1,2-propandiol, (I-menthoxy)-2-methyl-1,2-propandiol, I-menthyl-methylether), menthylesters (for example menthylformiate, menthylacetate, menthylisobutyrate, menthyllactates, L-menthyl-L-lactate, L-menthyl-D-lactate, menthyl-(2-methoxy)acetate, menthyl-(2-methoxyethoxy-)acetate, menthylpyroglutamate), menthylcarbonates (for example menthylpropyleneglycolcarbonate, menthylethyleneglycolcarbonate, menthylglycerolcarbonate or mixtures thereof), the semi-esters of menthols with a dicarboxylic acid or derivatives thereof (for example mono-menthylsuccinate, mono-menthylglutarate, mono-menthylmalonate, O-menthyl succinic acid ester-N,N-(dimethyl)amide, O-menthyl succinic acid ester amide), menthanecarboxylic acid amides (in this case preferably menthanecarboxylic acid-N-ethylamide [WS3] or N$^\alpha$-(menthanecarbonyl)glycmethylester [WS5], as described in U.S. Pat. No. 4,150,052, menthanecarboxylic acid-N-(4-cyanophenyl)amide or menthanecarboxylic acid-N-(4-cyanomethylphenyl)amide as described in WO 2005 049553 A1, methanecarboxylic acid-N-(alkoxyalkyl)amides), menthone and menthone derivatives (for example L-menthone glycerol ketal), 2,3-dimethyl-2-(2-propyl)-butyric acid derivatives (for example 2,3-dimethyl-2-(2-propyl)-butyric acid-N-methylamide [WS23]), isopulegol or its esters (I-(–)-isopulegol, I-(–)-isopulegolacetate), menthane derivatives (for example p-menthane-3,8-diol), cubebol or synthetic or natural mixtures, containing cubebol, pyrrolidone derivatives of cycloalkyldione derivatives (for example 3-methyl-2(1-pyrrolidinyl)-2-cyclopentene-1-one) or tetrahydropyrimidine-2-one (for example iciline or related compounds, as described in WO 2004/026840), further carboxamides (for example N-(2-(pyridin-2-yl)ethyl)-3-p-menthanecarboxamide or related compounds), (1R,2S,5R)—N-(4-Methoxyphenyl)-5-methyl-2-(1-isopropyl)cyclohexane-carboxamide [WS12], oxamates (preferably those described in EP 2033688 A2).

O. Anti-Microbial Agents

Suitable anti-microbial agents are, in principle, all substances effective against Gram-positive bacteria, such as, for example, 4-hydroxybenzoic acid and its salts and esters, N-(4-chlorophenyl)-N'-(3,4-dichlorophenyl)urea, 2,4,4'-trichloro-2'-hydroxy-diphenyl ether (triclosan), 4-chloro-3,5-dimethyl-phenol, 2,2'-methylenebis(6-bromo-4-chlorophenol), 3-methyl-4-(1-methylethyl)phenol, 2-benzyl-4-chloro-phenol, 3-(4-chlorophenoxy)-1,2-propanediol, 3-iodo-2-propynyl butylcarbamate, chlorhexidine, 3,4,4'-trichlorocarbanilide (TTC), antibacterial fragrances, thymol, thyme oil, eugenol, oil of cloves, menthol, mint oil, farnesol, phenoxyethanol, glycerol monocaprate, glycerol monocaprylate, glycerol monolaurate (GML), diglycerol monocaprate (DMC), salicylic acid N-alkylamides, such as, for example, n-octylsalicylamide or n-decylsalicylamide.

P. Enzyme Inhibitors

Suitable enzyme inhibitors are, for example, esterase inhibitors. These are preferably trialkyl citrates, such as trimethyl citrate, tripropyl citrate, triisopropyl citrate, tributyl citrate and, in particular, triethyl citrate (Hydagen CAT). The substances inhibit enzyme activity, thereby reducing the formation of odour. Other substances which are suitable esterase inhibitors are sterol sulfates or phosphates, such as, for example, lanosterol, cholesterol, campesterol, stigmasterol and sitosterol sulfate or phosphate, dicarboxylic acids and esters thereof, such as, for example, glutaric acid, monoethyl glutarate, diethyl glutarate, adipic acid, monoethyl adipate, diethyl adipate, malonic acid and diethyl malonate, hydroxycarboxylic acids and esters thereof, such as, for example, citric acid, malic acid, tartaric acid or diethyl tartrate, and zinc glycinate.

Q. Odour Absorbers and Antiperspirant Active Agents

Suitable odour absorbers are substances which are able to absorb and largely retain odour-forming compounds. They lower the partial pressure of the individual components, thus also reducing their rate of diffusion. It is important that perfumes must remain unimpaired in this process. Odour absorbers are not effective against bacteria. They comprise, for example, as main constituent, a complex zinc salt of ricinoleic acid or specific, largely odour-neutral fragrances which are known to the person skilled in the art as "fixatives", such as, for example, extracts of labdanum or *styrax* or certain abietic acid derivatives. The odour masking agents are fragrances or perfume oils, which, in addition to their function as odour masking agents, give the deodorants their respective fragrance note. Perfume oils which may be mentioned are, for example, mixtures of natural and synthetic fragrances. Natural fragrances are extracts from flowers, stems and leaves, fruits, fruit peels, roots, woods, herbs and grasses, needles and branches, and resins and balsams. Also suitable are animal products, such as, for example, civet and castoreum. Typical synthetic fragrance compounds are products of the ester, ether, aldehyde, ketone, alcohol, and hydrocarbon type. Fragrance compounds of the ester type are, for example, benzyl acetate, p-tert-butylcyclohexyl acetate, linalyl acetate, phenylethyl acetate, linalyl benzoate, benzyl formate, allyl cyclohexylpropionate, styrallyl propionate and benzyl salicylate. The ethers include, for example, benzyl ethyl ether, and the aldehydes include, for example, the linear alkanals having 8 to 18 carbon atoms, citral, citronellal, citronelly-loxyacetaldehyde, cyclamen aldehyde, hydroxycitronellal, lilial and bourgeonal, the ketones include, for example, the ionones and methyl cedryl ketone, the alcohols include anethole, citronellol, eugenol, isoeugenol, geraniol, linaool, phenylethyl alcohol and terpineol, and the hydrocarbons include mainly the terpenes and balsams. Preference is, however, given to using mixtures of different fragrances which together produce a pleasing fragrance note. Essential oils of relatively low volatility, which are mostly used as aroma components, are also suitable as perfume oils, e.g. sage oil, camomile oil, oil of cloves, *melissa* oil, mint oil, cinnamon leaf oil, linden flower oil, juniperberry oil, vetiver oil, olibanum oil, galbanum oil, labdanum oil and lavandin oil. Preference is given to using bergamot oil, dihydromyrcenol, lilial, lyral, citronellol, phenylethyl alcohol, α-hexylcinnamaldehyde, geraniol, benzylacetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix coeur, iso-E-super, Fixolide NP, evernyl, iraldein gamma, phenylacetic acid, geranyl acetate, benzyl acetate, rose oxide, romilat, irotyl and floramat alone or in mixtures.

Suitable astringent antiperspirant active ingredients are primarily salts of aluminium, zirconium or of zinc. Such suitable antihydrotic active ingredients are, for example, aluminium chloride, aluminium chlorohydrate, aluminium dichlorohydrate, aluminium sesquichlorohydrate and complex compounds thereof, e.g. with 1,2-propylene glycol, aluminium hydroxyallantoinate, aluminium chloride tartrate, aluminium zirconium trichlorohydrate, aluminium zirconium tetrachlorohydrate, aluminium zirconium pentachlorohydrate and complex compounds thereof, e.g. with amino acids, such as glycine.

R. Film Formers and Anti-Dandruff Agents

Standard film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds.

Suitable antidandruff agents are Pirocton Olamin (1-hydroxy-4-methyl-6-(2,4,4-trimethylpentyl)-2-(1H)-pyridinone monoethanolamine salt), Baypival® (Climbazole), Ketoconazol® (4-acetyl-1-{4-[2-(2,4-dichlorophenyl) r-2-(1H-imidazol-1-ylmethyl)-1,3-dioxylan-c-4-ylmethoxyphenyl}-piperazine, ketoconazole, elubiol, selenium disulfide, colloidal sulfur, sulfur polyethylene glycol sorbitan monooleate, sulfur ricinol polyethoxylate, sulfur tar distillate, salicylic acid (or in combination with hexachlorophene), undecylenic acid, monoethanolamide sulfosuccinate Na salt, Lamepon® UD (protein/undecylenic acid condensate), zinc pyrithione, aluminium pyrithione and magnesium pyrithione/dipyrithione magnesium sulfate.

S. Carriers and Hydrotropes

Preferred cosmetics carrier materials are solid or liquid at 25° C. and 1013 mbar (including highly viscous substances) as for example glycerol, 1,2-propylene glycol, 1,2-butylene glycol, 1,3-propylene glycol, 1,3-butylene glycol, ethanol, water and mixtures of two or more of said liquid carrier materials with water. Optionally, these preparations according to the invention may be produced using preservatives or solubilizers. Other preferred liquid carrier substances, which may be a component of a preparation according to the invention are selected from the group consisting of oils such as vegetable oil, neutral oil and mineral oil.

Preferred solid carrier materials, which may be a component of a preparation according to the invention are hydrocolloids, such as starches, degraded starches, chemically or physically modified starches, dextrins, (powdery) maltodextrins (preferably with a dextrose equivalent value of 5 to 25, preferably of 10-20), lactose, silicon dioxide, glucose, modified celluloses, gum arabic, ghatti gum, traganth, karaya, carrageenan, pullulan, curdlan, xanthan gum, gellan gum, guar flour, carob bean flour, alginates, agar, pectin and inulin and mixtures of two or more of these solids, in particular maltodextrins (preferably with a dextrose equivalent value of 15-20), lactose, silicon dioxide and/or glucose.

In addition, hydrotropes, for example ethanol, isopropyl alcohol or polyols, may be used to improve flow behaviour. Suitable polyols preferably contain 2 to 15 carbon atoms and at least two hydroxyl groups. The polyols may contain other functional groups, more especially amino groups, or may be modified with nitrogen. Typical examples are glycerol;

alkylene glycols such as, for example, ethylene glycol, diethylene glycol, propylene glycol, butylene glycol, hexylene glycol and polyethylene glycols with an average molecular weight of 100 to 1000 Dalton;

technical oligoglycerol mixtures with a degree of self-condensation of 1.5 to 10, such as for example technical diglycerol mixtures with a diglycerol content of 40 to 50% by weight;

methylol compounds such as, in particular, trimethylol ethane, trimethylol propane, trimethylol butane, pentaerythritol and dipentaerythritol;

lower alkyl glucosides, particularly those containing 1 to 8 carbon atoms in the alkyl group, for example methyl and butyl glucoside;

sugar alcohols containing 5 to 12 carbon atoms, for example sorbitol or mannitol, sugars containing 5 to 12 carbon atoms, for example glucose or sucrose;

amino sugars, for example glucamine;

dialcoholamines, such as diethanolamine or 2-aminopropane-1,3-diol.

T. Preservatives

Suitable preservatives are, for example, phenoxyethanol, formaldehyde solution, parabens, pentanediol or sorbic acid and the other classes of compounds listed in Appendix 6, Parts A and B of the Kosmetikverordnung ("Cosmetics Directive").

U. Perfume Oils and Fragrances

Suitable perfume oils are mixtures of natural and synthetic perfumes. Natural perfumes include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamom, *costus*, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones, ⍺-isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable perfume. Other suitable perfume oils are essential oils of relatively low volatility which are mostly used as aroma components. Examples are sage oil, camomile oil, clove oil, *melissa* oil, mint oil, cinnamon leaf oil, lime-blossom oil, juniper berry oil, vetiver oil, olibanum oil, galbanum oil, ladanum oil and lavendin oil. The following are preferably used either individually or in the form of mixtures: bergamot oil, dihydromyrcenol, lilial, lyral, citronellol, phenylethyl alcohol, hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

V. Dyes

Suitable dyes are any of the substances suitable and approved for cosmetic purposes as listed, for example, in the publication "Kosmetische Färbemittel" of the Farbstoff-kommission der Deutschen Forschungsgemeinschaft, Verlag Chemie, Weinheim, 1984, pages 81 to 106. Examples include cochineal red A (C.I. 16255), patent blue V (C.I. 42051), indigotin (C.I. 73015), chlorophyllin (C.I. 75810), quinoline yellow (C.I. 47005), titanium dioxide (C.I. 77891), indanthrene blue RS (C.I. 69800) and madder lake (C.I. 58000). Luminol may also be present as a luminescent dye. Advantageous coloured pigments are for example titanium dioxide, mica, iron oxides (e.g. $Fe_2O_3$ $Fe_3O_4$, $FeO(OH)$) and/or tin oxide. Advantageous dyes are for example carmine, Berlin blue, chromium oxide green, ultramarine blue and/or manganese violet.

Preferred compositions according to the present inventions are selected from the group of products for treatment, protecting, care and cleansing of the skin and/or hair or as a make-up product, preferably as a leave-on product (meaning that the one or more compounds of formula (I) stay on the skin and/or hair for a longer period of time, compared to rinse-off products, so that the moisturizing and/or anti-ageing and/or wound healing promoting action thereof is more pronounced).

The formulations according to the invention are preferably in the form of an emulsion, e.g. W/O (water-in-oil), O/W (oil-in-water), W/O/W (water-in-oil-in-water), O/W/O (oil-in-water-in-oil) emulsion, PIT emulsion, Pickering emulsion, emulsion with a low oil content, micro- or nanoemulsion, a solution, e.g. in oil (fatty oils or fatty acid esters, in particular $C_6$-$C_{32}$ fatty acid $C_2$-$C_{30}$ esters) or silicone oil, dispersion, suspension, creme, lotion or milk, depending on the production method and ingredients, a gel (including hydrogel, hydrodispersion gel, oleogel), spray (e.g. pump spray or spray with propellant) or a foam or an impregnating solution for cosmetic wipes, a detergent, e.g. soap, synthetic detergent, liquid washing, shower and bath preparation, bath product (capsule, oil, tablet, salt, bath salt, soap, etc.), effervescent preparation, a skin care product such as e.g. an emulsion (as described above), ointment, paste, gel (as described above), oil, balsam, serum, powder (e.g. face powder, body powder), a mask, a pencil, stick, roll-on, pump, aerosol (foaming, non-foaming or post-foaming), a deodorant and/or antiperspirant, mouthwash and mouth rinse, a foot care product (including keratolytic, deodorant), an insect repellent, a sunscreen, after-sun preparation, a shaving product, aftershave balm, pre- and aftershave lotion, a depilatory agent, a hair care product such as e.g. shampoo (including 2-in-1 shampoo, anti-dandruff shampoo, baby shampoo, shampoo for dry scalps, concentrated shampoo), conditioner, hair tonic, hair water, hair rinse, styling creme, pomade, perm and setting lotion, hair spray, styling aid (e.g. gel or wax), hair smoothing agent (detangling agent, relaxer), hair dye such as e.g. temporary direct-dyeing hair dye, semi-permanent hair dye, permanent hair dye, hair conditioner, hair mousse, eye care product, make-up, make-up remover or baby product.

The formulations according to the invention are particularly preferably in the form of an emulsion, in particular in the form of a W/O, O/W, W/O/W, O/W/O emulsion, PIT emulsion, Pickering emulsion, emulsion with a low oil content, micro- or nanoemulsion, a gel (including hydrogel, hydrodispersion gel, oleogel), a solution e.g. in oil (fatty oils or fatty acid esters, in particular $C_6$-$C_{32}$ fatty acid $C_2$-$C_{30}$ esters)) or silicone oil, or a spray (e.g. pump spray or spray with propellant).

Auxiliary substances and additives can be included in quantities of 5 to 99% b.w., preferably 10 to 80% b.w., based on the total weight of the formulation. The amounts of cosmetic or dermatological auxiliary agents and additives and perfume to be used in each case can easily be determined by the person skilled in the art by simple trial and error, depending on the nature of the particular product.

The preparations can also contain water in a quantity of up to 99% b.w., preferably 5 to 80% b.w., based on the total weight of the preparation.

Pharmaceutical Compositions

Another embodiment of the present invention refers to a pharmaceutical composition comprising the new ginger extract, containing the extract in an amount of from about 0.01 to about 1, preferably from about 0.1 to about 0.5% b.w.—calculated on the total composition.

Pharmaceutical compositions according to the present invention may include similar additives as already explained for the cosmetic application, such as for example oil bodies or emulsifiers and in particular co-actives supporting the beneficial properties of the new ginger extracts. It should also be mentioned that several actives cited in the following can also be incorporated in cosmetic formulations, so-called "cosmeceuticals". Therefore, the border between cosmetic and pharmaceutical compositions is in flow and it should be understood that components cited for one application are recommended for the other mutatis-mutandis without literal repetition.

A. Anti-Irritation Agents

An important group of co-actives encompass anti-irritant agents such as for example steroidal anti-inflammatory substances of the corticosteroid type, such as e.g. hydrocortisone, hydrocortisone derivatives, such as hydrocortisone 17-butyrate, dexamethasone, dexamethasone phosphate, methylprednisolone or cortisone; non-steroidal anti-inflammatories like oxicams, such as piroxicam or tenoxicam; salicylates, such as aspirin, Disalcid, Solprin or fendosal; acetic acid derivatives, such as diclofenac, fenclofenac, indomethacin, sulindac, tolmetin or clindanac; fenamates, such as mefenamic, meclofenamic, flufenamic or niflumic; propionic acid derivatives, such as ibuprofen, naproxen or benoxaprofen, or pyrazoles, such as phenylbutazone, oxyphenylbutazone, febrazone or azapropazone. Alternatively, natural anti-inflammatory substances or reddening- and/or itching-alleviating substances can be employed. Plant extracts, specific highly active plant extract fractions and highly pure active substances isolated from plant extracts, can be employed like extracts, fractions and active substances from *aloe vera, Commiphora* species, *Rubia* species, *Rubus* species, willow, rose-bay, willowherb, oats, *calendula, arnica*, St. John's wort, honeysuckle, ginger, chamomile, rosemary, sage, *melissa, Passiflora incarnata, Sophora japonica*, witch hazel, *Pueraria, Dianthus* or *Echinacea*, as well as pure substances, such as, inter alia, bisabolol, apigenin, apigenin-7-glucoside, rosmarinic acid, boswellic acid, phytosterols, glycyrrhizic acid, glabridin, licochalcone A, [6]-paradol, and anthranilic acid amides, such as, in particular, avenanthramides or dianthramides, are particularly preferred. The total amount of anti-irritants in a formulation or product according to the invention is preferably in the range of from 0.0001 to 20 wt. %, preferably from 0.0001 to 10 wt. %, in particular from 0.001 to 5 wt. %, based on the total weight of the formulation or product, respectively.

Particular useful co-actives are selected from the group consisting of anti-mycotica and pain relief agents, and more particularly the group consisting of erythromycin, dimetindene, betamethasone, ibuprofen, ketoprofene, diclofenac, metronidazole, acyclovir, imiquimod, terbinafine, docosanol, cyclopyroxolamine, and their mixtures:

(I) Erythromycin is a macrolide antibiotic that has an antimicrobial spectrum similar to or slightly wider than that of penicillin, and is often used for people who have an allergy to penicillin.

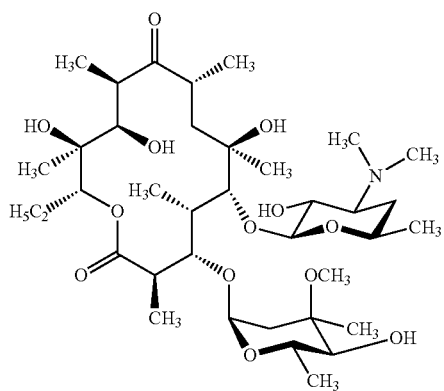

Recent studies have also shown that it can be used as a mild anti-depressant. For respiratory tract infections, it has better coverage of atypical organisms, including *Mycoplasma* and legionellosis. It was first marketed by Eli Lilly and Company, and it is today commonly known as EES (erythromycin ethylsuccinate, an ester prodrug that is commonly administered). In structure, this macrocyclic compound contains a 14-membered lactone ring with ten asymmetric centres and two sugars (L-cladinose and D-desosamine), making it a compound very difficult to produce via synthetic methods. Erythromycin is produced from a strain of the actinomycete *Saccharopolyspora erythraea* (see U.S. Pat. No. 2,653,899—Eli Lily).

(II) Dimetindene, also known as Fenistil (RS-dimethyl(2-(3-[pyridin-2-yl)ethyl]-1H-inden-2-yl)ethyl)amine) is an antihistamine/anticholinergic used orally and locally as an antipruritic.

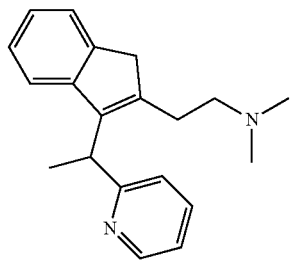 [SMILES: CC(C1=C(CCN(C)C)Cc2ccccc21)c1ccccn1]

(III) Betamethasone (8S,9R,10S,11S,13S,14S,16S,17R)-9-fluoro-11,17-(2-hydroxyacetyl)-10,13,16-trimethyl-6,7,8,9,10,11,12,13,14,15,16,17-dodecahydro-3H-cyclopenta (alpha)-phenanthren-3-one) is a potent glucocorticoid steroid with anti-inflammatory and immunosuppressive properties.

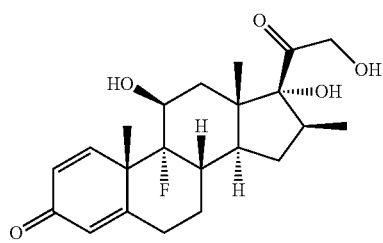

Unlike other drugs with these effects, betamethasone does not cause water retention. It is applied as a topical cream, ointment, foam, lotion or gel to treat itching. Betamethasone sodium phosphate is sometimes prescribed as an intramuscular injection (I.M) for itching from various ailments, including allergic reactions to poison ivy and similar plants (see U.S. Pat. No. 3,053,865—Merck).

(IV) Ibuprofen (RS)-2-(4-(2-methylpropyl)phenyl)propanoic acid) from the nomenclature isobutyl-propanoic-phenolic acid) is a non-steroidal anti-inflammatory drug (NSAID) used for relief of symptoms of arthritis, fever, as an analgesic (pain reliever), especially where there is an inflammatory component, and dysmenorrhea.

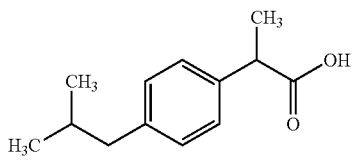

Ibuprofen is known to have an antiplatelet effect, though it is relatively mild and somewhat short-lived when compared with aspirin or other better-known antiplatelet drugs. In general, ibuprofen also acts as a vasoconstrictor, having been shown to constrict coronary arteries and some other blood vessels mainly because it inhibits the vasodilating prostacyclin produced by cyclooxygenase 2 enzymes. Ibuprofen was derived from propanoic acid by the research arm of Boots Group during the 1960s and was patented in 1961. Originally marketed as Brufen, ibuprofen is available under a variety of popular trademarks, including Motrin, Nurofen, Advil, and Nuprin (see U.S. Pat. No. 3,385,886—Boots).

(V) Ketoprofen (RS)2-(3-benzoylphenyl)-propionic acid is another one of the propionic acid class of non-steroidal anti-inflammatory drug (NSAID) with analgesic and antipyretic effects.

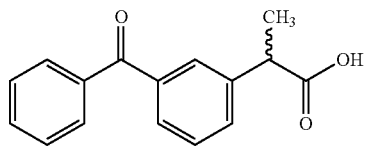 [SMILES: CC(C(=O)O)c1cccc(C(=O)c2ccccc2)c1]

It acts by inhibiting the body's production of prostaglandins (see U.S. Pat. No. 3,641,127—Rhone-Poulenc).

(VI) Diclofenac is also a non-steroidal anti-inflammatory drug (NSAID) taken to reduce inflammation and as an analgesic reducing pain in certain conditions.

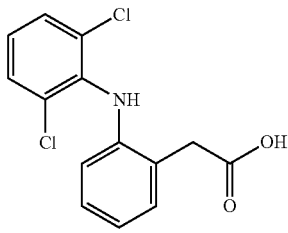 [SMILES: O=C(O)Cc1ccccc1Nc1c(Cl)cccc1Cl]

The name is derived from its chemical name: 2-(2,6-dichloranilino) phenylacetic acid. In the United Kingdom, India, Brazil and the United States, it may be supplied as either the sodium or potassium salt, in China most often as the sodium salt, while in some other countries only as the potassium salt. Diclofenac is available as a generic drug in a number of formulations. Over-the-counter (OTC) use is approved in some countries for minor aches and pains and fever associated with common infections (see U.S. Pat. No. 3,558,690—Ciba-Geigy).

(VII) Metronidazole (2-(2-methyl-5-nitro-1H-imidazol-1-yl)ethanol) is a nitroimidazole antibiotic medication used particularly for anaerobic bacteria and protozoa.

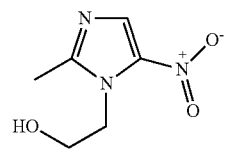

Metronidazole is an antibiotic, amebicide, and antiprotozoal. It is the drug of choice for first episodes of mild-to-moderate *Clostridium difficile* infection. It is marketed in the U.S.A. by Pfizer and globally by Sanofiunder the trade name Flagyl, in Pakistan and Bangladesh also as Nidagyl by Star Laboratories, and in Thailand, as Mepagyl by That Nakhorn Patana. It is also marketed in UK by Milpharm Limited and Almus Pharmaceuticals. Metronidazole was developed in 1960. Metronidazole is used also as a gel preparation in the treatment of the dermatological conditions such as rosaceae and fungating tumours (see U.S. Pat. No. 2,944,061—Rhone Poulenc).

(VIII) Acyclovir or acyclovir (USAN, former BAN), chemical name acycloguanosine (2-Amino-1,9-dihydro-9-((2-hydroxyethoxy)methyl)-6H-Purin-6-one), abbreviated as ACV is a guanosine analogue antiviral drug, marketed under trade names such as Cyclovir, Herpex, Acivir, Acivirax, Zovirax, and Xovir. The solid active agent has a solubility in water (20° dH) at 20° C. of less than 5 g/L.

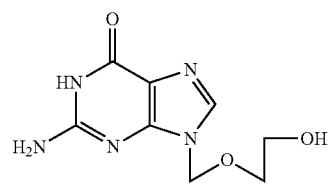 [SMILES: Nc1nc2c(ncn2COCCO)c(=O)[nH]1]

One of the most commonly used antiviral drugs; it is primarily used for the treatment of herpes simplex virus infections, as well as in the treatment of varicella zoster (chickenpox) and herpes zoster (shingles); see also U.S. Pat. No. 4,199,574 (Wellcome).

(IX) Imiquimod (3-(2-methylpropyl)-3,5,8-triazatricyclo [7.4.0.0.$^{2,6}$]trideca-1(9),2(6),4,7,10,12-hexaen-7-amine, INN) is a prescription medication that acts as an immune response modifier.

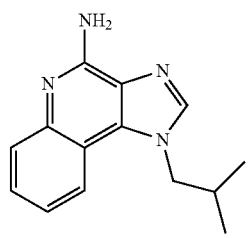 [SMILES: CC(C)Cn1cnc2c(N)nc3ccccc3c21]

It is marketed by Meda AB, Graceway Pharmaceuticals and iNova Pharmaceuticals under the trade names Aldara and Zyclara, and by Mochida as Beselna. It is also referred to as R-837 (see U.S. Pat. No. 4,689,338—Riker).

(X) Terbinafine, more particularly terbinafine hydrochloride [(2E)-6,6-dimethylhept-2-en-4-yn-1-yl](methyl)(naphthalen-1-ylmethyl)amine) is a synthetic allylamine antifungal from Novartis. It is highly lipophilic in nature and tends to accumulate in skin, nails, and fatty tissues.

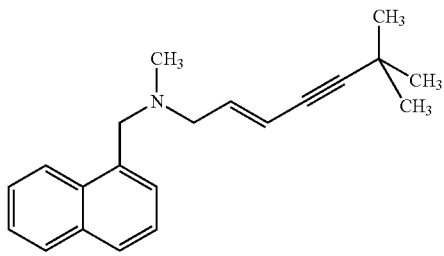 [SMILES: CN(C/C=C/C#CC(C)(C)C)Cc1cccc2ccccc12]

It is sold by the name Lamisil in Argentina, Australia, Belgium, Brazil, Canada, Chile, Egypt, Finland, France, Germany, Greece, Hungary, Iceland, Ireland, Israel, Mexico, Pakistan, Peru, New Zealand, Norway, Romania, Russia, Slovenia, South Africa, Sweden, United Kingdom, United States and Venezuela, also sold under the name Corbinal and Terbisil in Turkey and under the name "undofen cream" in Poland. As a generic it is sold under the name Zabel in Australia. It is also available as a generic medication in the United States, United Kingdom, Belgium, Switzerland and Brazil. In India, Terbinafine hydrochloride is available in topical form under the brand name Sebifin (Ranbaxy Labs), Zimig (GSK Pharma) and mycoCeaze (Progreś Laboratories).MycoVa, developed by Apricus Biosciences, is a topical nail solution of terbinafine and DDAIP which has completed three Phase III studies for the treatment of onychomycosis (see U.S. Pat. No. 4,755,534—Sandoz)

(XI) Docosanol, also known as behenyl alcohol, is a saturated fatty alcohol used traditionally as an emollient, emulsifier, and thickener in cosmetics, nutritional supplement (as an individual entity and also as a constituent of policosanol), and more recently, in a Food and Drug Administration (FDA) approved pharmaceutical, Abreva, approved as an antiviral agent for reducing the duration of cold sores caused by the herpes simplex virus.

(XII) Ciclopiroxolamine (6-cyclohexyl-1-hydroxy-4-methylpyridin-2(1H)-one) also called Batrafen, Loprox, Mycoster, Penlac and Stieprox, is a synthetic antifungal agent for topical dermatologic treatment of superficial mycoses.

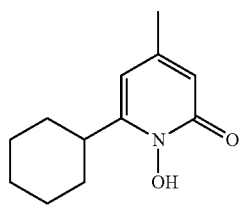

It is most useful against Tinea versicolor (see U.S. Pat. No. 3,883,545—Merck).

B. Anti-Cellulite Agents

Anti-cellulite agents and lipolytic agents are preferably selected from the group consisting of those described in WO 2007/077541, and beta-adrenergic receptor agonists such as Synephrine and its derivatives, and cyclohexyl carbamates described in WO 2010/097479.

Agents enhancing or boosting the activity of anti-cellulite agents, in particular agents which stimulate and/or depolarise C nerve fibres, are preferably selected from the group consisting of capsaicin and derivatives thereof, vanillyl-nonylamid and derivatives thereof, L-carnitine, coenzym A, isoflavonoides, soy extracts, *ananas* extract and conjugated linoleic acid.

C. Fat Enhancing Agents

Formulations and products according to the present invention may also comprise one or more fat enhancing and/or adipogenic agents as well as agents enhancing or boosting the activity of fat enhancing agents. A fat enhancing agent is for example hydroxymethoxy-phenyl propylmethylmethoxy-benzofuran (trade name: Sym3D®).

D. Hair Growth Activators or Inhibitors

Formulations and products according to the present invention may also comprise one or more hair growth activators, i.e. agents to stimulate hair growth. Hair growth activators are preferably selected from the group consisting of pyrimidine derivatives such as 2,4-diaminopyrimidine-3-oxide (Aminexil), 2,4-diamino-6-piperidinopyrimidine-3-oxide (Minoxidil) and derivatives thereof, 6-amino-1,2-dihydro-1-hydroxy-2-imino-4-piperidinopyrimidine and its derivatives, xanthine alkaloids such as caffeine, theobromine and theophylline and derivatives thereof, quercetin and derivatives, dihydroquercetin (taxifolin) and derivatives, potassium channel openers, antiandrogenic agents, synthetic or natural 5-reductase inhibitors, nicotinic acid esters such as tocopheryl nicotinate, benzyl nicotinate and C1-C6 alkyl nicotinate, proteins such as for example the tripeptide Lys-Pro-Val, diphencypren, hormons, finasteride, dutasteride, flutamide, bicalutamide, pregnane derivatives, progesterone and its derivatives, cyproterone acetate, spironolactone and other diuretics, calcineurin inhibitors such as FK506 (Tacrolimus, Fujimycin) and its derivatives, Cyclosporin A and derivatives thereof, zinc and zinc salts, polyphenols, procyanidins, proanthocyanidins, phytosterols such as for example beta-sitosterol, biotin, eugenol, (±)-beta-citronellol, panthenol, glycogen for example from mussels, extracts from microorganisms, algae, plants and plant parts of for example the genera dandelion (*Leontodon* or *Taraxacum*), *Orthosiphon, Vitex, Coffea, Paullinia, Theobroma, Asiasarum, Cucurbita* or *Styphnolobium, Serenoa repens* (saw palmetto), *Sophora flavescens, Pygeum africanum, Panicum miliaceum, Cimicifuga racemosa, Glycine max, Eugenia caryophyllata, Cotinus coggygria, Hibiscus rosa-sinensis, Camellia sinensis, Ilex paraguariensis, Isochrysis galbana*, licorice, grape, apple, barley or hops or/nd hydrolysates from rice or wheat.

Alternatively, formulations and products according to the present invention may comprise one or more hair growth inhibitors (as described above), i.e. agents to reduce or prevent hair growth. Hair growth inhibitors are preferably selected from the group consisting of activin, activin derivatives or activin agonists, ornithine decarboxylase inhibitors such as alpha-difluoromethylornithine or pentacyclic triterpenes like for example ursolic acid, betulin, betulinic acid, oleanolic acid and derivatives thereof, 5alpha-reductase inhibitors, androgen receptor antagonists, S-adenosylmethionine decarboxylase inhibitors, gamma-glutamyl transpeptidase inhibitors, transglutaminase inhibitors, soybean-derived serine protease inhibitors, extracts from microorganisms, algae, different microalgae or plants and plant parts of for example the families Leguminosae, Solanaceae, Graminae, Asclepiadaceae or Cucurbitaceae, the genera *Chondrus, Gloiopeltis, Ceramium, Durvillea, Glycine max, Sanguisorba officinalis, Calendula officinalis, Hamamelis virginiana, Arnica montana, Salix alba, Hypericum perforatum* or *Gymnema sylvestre*.

E. Solutes

Formulations and products according to the present invention may also comprise one or more compatible solutes. Preferred compatible solutes are such as described in WO 01/76572, particularly dimyo-inositol phosphate (DIP), diglycerin phospate (DGP), di-myoinositol phosphate (DIP), cyclic 2,3 diphosphoglycerate (cDPG), 1,1-di-glycerol phosphate (DGP), beta-mannosyl glycerate (firoin), beta-mannosyl glyceramide (firoin-A) and dimannosyl-di-inositol phosphate (DMIP) and ectoine and ectoine-derivatives, as described in EP 0 553 884, EP 0 671 161 and WO 94/15923, in particular ((S)-1,4,5,6-tetrahydro-2-methyl-4-pyrimidinecarboxylic acid) and hydroxyectoine ((S,S)-1,4,5,6-tetrahydro-5-hydroxy-2-methyl-4-pyrinnidinecarboxylic acid). Preferably, the total amount of compatible solutes is in the range of from 0.05 to 10 wt.-%, preferably from 0.1 to 5 wt.-%, based on the total weight of the formulation or product.

F. Solvents

The pharmaceutical compositions may contain such as for example aliphatic alcohols or 1,2-alkandiols or of course simply water. Suitable aliphatic alcohols are selected from the group consisting of ethanol, n-propanol, isopropylalcohol, the isomeric butanols and their mixtures. The preferred species is ethanol, in particular with a purity of at least 95%. Suitable 1,2-alkandiols encompass 1,2-butadiol, 1,2-pentandiol, 1,2-hexandiol, 1,2-heptanddiol, 1,2-octandiol, 1,2-nonandiol, 1,2-decandiol, 1,2-undecandiol, 1,2,dodecandiol and their mixtures. The preferred 1,2-alkandiol is 1,2-pentandiol.

Oral Compositions

Another embodiment of the present invention refers to an oral composition comprising the new ginger extract, containing the extract in an amount of from about 0.01 to about 1, preferably from about 0.1 to about 0.5% b.w.—calculated on the total composition. Oral compositions are intended to be brought into contact with the oral cavity, for example in the form of toothpastes, dental gels, dental creams, mouth washes, sugar-free candies for sucking, oral sprays, dental floss or dental care chewing gums. That is why they are also considered to be dental compositions. The term does not encompass food products dedicated for nutrition.

The oral compositions of the present invention typically comprise an abrasive system (abrasive or polishing agent), such as e.g. silicas, calcium carbonates, calcium phosphates, aluminium oxides and/or hydroxyapatites, surface-active substances, such as e.g. sodium lauryl sulfate, sodium lauryl sarcosinate and/or cocamidopropyl betaine, moisture-retaining agents, such as e.g. glycerol and/or sorbitol, thickening agents, such as e.g. carboxymethylcellulose, polyethylene glycols, carrageenan and/or Laponite®, sweeteners, such as e.g. saccharin, flavour correctants for unpleasant taste impressions, flavour correctants for further, as a rule not unpleasant taste impressions, flavour-modulating substances (e.g. inositol phosphate, nucleotides, such as guanosine monophosphate, adenosine monophosphate or other substances, such as sodium glutamate or 2-phenoxypropionic acid), cooling active compounds, such as e.g. menthol derivatives (e.g. L-menthyl lactate, L-menthyl alkyl carbonates, menthone ketals, menthanecarboxylic acid amides), 2,2,2-trialkylacetic acid amides (e.g. 2,2-diisopropylpropionic acid methylamide), icilin and icilin derivatives, stabilizers and active compounds, such as e.g. sodium fluoride, sodium monofluorophosphate, tin difluoride, quaternary ammonium fluorides, zinc citrate, zinc sulfate, tin pyrophosphate, tin dichloride, mixtures of various pyrophosphates, triclosan, chlorhexidine, cetylpyridinium chloride, aluminium lactate, potassium citrate, potassium nitrate, potassium chloride, strontium chloride, hydrogen peroxide, aromas, sodium bicarbonate and/or odour correctants.

Formulations or products according to the invention in the form of chewing gums or, in particular, dental care chewing gums comprise chewing gum bases which comprise elastomers, such as, for example, polyvinyl acetates (PVA), polyethylenes, (low or medium molecular weight) polyisobutenes (PIB), polybutadienes, isobutene-isoprene copolymers (butyl rubber), polyvinyl ethyl ethers (PVE), polyvinyl butyl ethers, copolymers of vinyl esters and vinyl ethers, styrene/butadiene copolymers (styrene/butadiene rubber, SBR) or vinyl elastomers, e.g. based on vinyl acetate/vinyl laurate, vinyl acetate/vinyl stearate or ethylene/vinyl acetate, and mixtures of the elastomers mentioned, as described, for example, in EP 0 242 325, U.S. Pat. No. 4,518,615, U.S. Pat. No. 5,093,136, U.S. Pat. No. 5,266,336 U.S. Pat. No. 5,601,858 or U.S. Pat. No. 6,986,709. In addition, chewing gum bases comprise further constituents, such as, for example, sugars, sugar substitutes or sweet-tasting substances in particular those described in WO 2009/21558, (mineral) fillers, plasticizers, emulsifiers, antioxidants, waxes, fats or fatty oils, such as, for example, hardened (hydrogenated) plant or animal fats, and mono-, di- or triglycerides. Suitable (mineral) fillers are, for example, calcium carbonate, titanium dioxide, silicon dioxide, talc, aluminium oxide, dicalcium phosphate, tricalcium phosphate, magnesium hydroxide and mixtures thereof. Suitable plasticizers or agents for preventing sticking (detackifiers) are, for example, lanolin, stearic acid, sodium stearate, ethyl acetate, diacetin (glycerol diacetate), triacetin (glycerol triacetate) and triethyl citrate. Suitable waxes are, for example, paraffin waxes, candelilla wax, carnauba wax, microcrystalline waxes and polyethylene waxes. Suitable emulsifiers are, for example, phosphatides, such as lecithin, and mono- and diglycerides of fatty acids, e.g. glycerol monostearate.

Formulations or products according to the invention (in particular those which are in the form of an oral care formulation or product or in the form of a formulation) preferably additionally comprise one or more aroma and/or flavouring substances, such as essential oils and extracts, tinctures and balsams, such as, for example, anisole, basil oil, bergamot oil, bitter almond oil, camphor oil, citronella oil, lemon oil; Eucalyptus citriodora oil, eucalyptus oil, fennel oil, grapefruit oil, camomile oil, spearmint oil, caraway oil, lime oil, mandarin oil, nutmeg oil (in particular nutmeg blossom oil=maces oil, mace oil), myrrh oil, clove oil, clove blossom oil, orange oil, oregano oil, parsley (seed) oil, peppermint oil, rosemary oil, sage oil (clary sage, Dalmatian or Spanish sage oil), star aniseed oil, thyme oil, vanilla extract, juniper oil (in particular juniper berry oil), wintergreen oil, cinnamon leaf oil; cinnamon bark oil, and fractions thereof, or constituents isolated therefrom.

It is of particular advantage if said formulations or products comprise at least one aroma substance, preferably 2, 3, 4, 5, 6, 7, 8, 9, 10 or more aroma substances, chosen from the following group: menthol (preferably I-menthol and/or racemic menthol), anethole, anisole, anisaldehyde, anisyl alcohol, (racemic) neomenthol, eucalyptol (1,8-cineol), menthone (preferably L-menthone), isomenthone (preferably D-isomenthone), isopulegol, menthyl acetate (preferably L-menthyl acetate), menthyl propionate, carvone (preferably (−)-carvone, optionally as a constituent of a spearmint oil), methyl salicylate (optionally as a constituent of a wintergreen oil), eugenol acetate, isoeugenol methyl ether, beta-homocyclocitral, eugenol, isobutyraldehyde, 3-octanol, dimethyl sulfide, hexanol, hexanal, trans-2-hexenal, cis-3-hexenol, 4-terpineol, piperitone, linalool, 8-ocimenyl acetate, isoamyl alcohol, isovaleraldehyde, alpha-pinene, beta-pinene, linnonene (preferably D-linnonene, optionally as a constituent of an essential oil), piperitone, trans-sabinene hydrate, menthofuran, caryophyllene, germacrene D, cinnamaldehyde, mint lactone, thymol, gamma-octalactone, gamma-nonalactone, gamma-decalactone, (1,3E,5Z)-undecatriene, 2-butanone, ethyl formate, 3-octyl acetate, isoamyl isovalerate, cis- and trans-carvyl acetate, p-cymol, damascenone, damascone, cis-rose oxide, trans-rose oxide, fenchol, acetaldehyde diethyl acetal, 1-ethoxyethyl acetate, cis-4-heptenal, cis-jasmone, methyl dihydrojasmonate, 2'-hydroxypropiophenone, menthyl methyl ether, myrtenyl acetate, 2-phenylethyl alcohol, 2-phenylethyl isobutyrate, 2-phenylethyl isovalerate, geraniol, nerol and viridiflorol.

Medicaments

As shown in the experimental part, the new extracts show various surprising activities with regard to stem cell protection, anti-oxidation and anti-inflammation. Therefore, another object of the present invention is directed to a medicament comprising the new ginger extract for protecting stem cells and for inhibiting the cyclooxygenase-2 (COX-2) activity and prostaglandin ES release.

INDUSTRIAL APPLICATION

Another object of the present invention is a therapeutical method for preserving stem cells by oral administration of a working amount of the ginger extract of claim 1 to an individual.

Another object of the present invention is also a non-therapeutical method for preserving stem cells by topical administration of a working amount of the extract of claim 1 to skin or hair of an individual.

Finally, additional embodiments of the present invention are directed to the use of the new ginger extracts as a protection agents for stem cells.

as an anti-oxidants.

as anti-inflammation agents.

as an anti-aging agents, particularly for skin and hair.

EXAMPLES

Example 1

Fresh ginger roots were frozen at −18° C. and afterwards shredded and cut. This material was dried at 30° C. for 17 hours using a continuous flow dryer. The dried material was subjected to supercritical extraction with carbon dioxide at 35° C., 250 bar and a flow rate of 10 kg $CO_2$/h*kg raw material. A first fraction collected within the first three hours of the extraction process was discarded due to the high content of essential oil. A second fraction from 3 hours to 5 hours from the starting was collected after de-pressurizing process resulting in the ginger extract according to the present invention. 32 kg dried ginger root resulted in 1 kg ginger extract according to the invention.

The composition of the extract thus obtained is presented in Table 1. FIG. 1 shows a HPLC chromatogram of the extract.

TABLE 1

Composition of a ginger extract according to the invention (content in % b.w.)

| Component | Average content | Specification |
|---|---|---|
| [6]-gingerol | 27 | 25-30 |
| [8]-gingerol | 7 | 5-10 |
| [10]-gingerol | 7 | 5-10 |
| sum of gingerols | 41 | 35-50 |
| [6]-shogaol | 2.5 | 1.5-4 |
| [8]-shogaol | 1 | 0.3-1.3 |
| [10]-shogaol | 0.2 | 0.03-1 |
| sum of shogaols | 3.7 | less than 6 |
| zingerone | 0.05 | less than 1 |
| sum of pungent components | 45 | 42-50 |

Example 2

Stem Cell Protection

In Vitro

HHFSC (Human Hair Follicle Stem Cells) isolated from hair follicle bulge (Celprogen) were cultivated in culture ware pre-coated with Human Hair Follicle Stem Cell Extra-cellular Matrix (Celprogen). The cells were incubated 2 h prior to and 16 h after UVB irradiation with test compounds. Cells were irradiated with 25 ml/cm$^2$ UVB in the presence of buffer solution. Apoptosis induction was evaluated by caspase 3/7 protein expression (Caspase-Glo 3/7, Promega) and quantified by chemiluminescence measurement.

The inhibition of apoptosis induction in the presence of test substances was calculated according to the following equation:

Inhibition of apoptosis induction [%] =
$$100 - \left( \frac{RLU \text{ test substance} - RLU \text{ control without } UVB}{RLU \text{ control} - RLU \text{ control without } UVB} \times 100 \right)$$

The abbreviations have the following meanings:

RLU test substance:
RLU of the wells with test substance and with UVB irradiation RLU control:
RLU of the wells without test substance, but with UVB irradiation RLU control without UVB:
RLU of the wells without test substance and without UVB irradiation The results are shown in Table 2:

TABLE 2

Inhibition of apoptosis induction relative to control

| Test Substance | Concentration [% b.w.] | Inhibition of UV induced apoptosis [%] |
|---|---|---|
| Ginger pungent $CO_2$ extract (50% pungent components) | 0.0005 | 20.2 |
| Ginger $CO_2$ extract (30% pungent components) | 0.002 | 22.6 |
| Ginger Hexan/Isopropanol 8:2 extract | 0.002 | 18.0 |

TABLE 2-continued

Inhibition of apoptosis induction relative to control

| Test Substance | Concentration [% b.w.] | Inhibition of UV in- duced apoptosis [%] |
|---|---|---|
| Ginger ethanol/water 1:1 extract | 0.002 | 18.4 |
| Ginger water extract | 0.002 | 12.4 |

Due to the lower concentration the ginger extract according to the present invention is the most potent inhibitor of UV induced apoptosis.

Example 3

COX-2-Assay

In Vitro

Cyclooxygenase-2 (COX-2) in the presence of test substance was mixed with the fluorometric substrate 10-acetyl-3,7-dihydroxyphenoxanin (ADHP) and Heme. The reaction was started by addition of the substrate arachidonic acid.

COX-2 converted the arachidonic acid into the prostaglandin endoperoxide G2 (PGG2). PGG2 was reduced to the corresponding alcohol PGH2. During this reaction ADHP resulted in fluorescent resorufin. Resorufin was quantified at an extinction wavelength of 535 nm and an emission wavelength of 590 nm.

The inhibition of COX-2 activity in the presence of test substances was calculated according to the following equation:

$$\text{Inhibition of } COX\text{-}2\ [\%] = 100 - \left(\frac{\text{Resorufin test substance} - \text{Resorufin control without } COX\text{-}2}{\text{Resorufin control} - \text{Resorufin control without } COX\text{-}2} \times 100\right)$$

The abbreviations have the following meanings:

Resorufin test substance:

Resorufin concentration of the wells with test substance and with COX-2

Resorufin control:

Resorufin concentration of the wells without test substance, but with COX-2

Resorufin control without COX-2:

Resorufin concentration of the wells without test substance and without COX-2

From the inhibition of the COX-2 [%] in a series of dilutions of tested samples the IC50 was calculated. This was the concentration at which the activity of the COX-2 was inhibited by 50%. The results are shown in Table 3:

TABLE 3

COX-2 inhibition (mean value of at least 2 independent tests)

| Test Substance | IC$_{50}$ |
|---|---|
| Ginger extract BIO3040 | 0.0005% |

Example 4

PGE2 Assay

In Vitro

Normal human epidermal keratinocytes (Lonza) are seeded in a 96-well microtiter plate at a concentration of $1.2 \times 10^4$ cells/well. Incubation for 20 to 24 h takes place at 37° C., 5% CO2, saturated humidity until growth to 50-60% confluency. Various concentrations of the test substances are applied to the cells in culture media. After incubation for 30 min the stimulation with 1 µM A23187 Calcium Ionophor (except for an unstimulated control) is started. After another 30 min of incubation, 50 µL of the supernatants are taken for the quantification of PGE2 using the competitive ELISA (PGE2 Biotrak EIA System, RPN222, Fa. GE Healthcare).

The percent bound for each standard and unknown substance is calculated using the following equation:

$$\% \ B/B_0 = \frac{A_{standard\ or\ test\ substance} - A_{blank}}{A_{zero\ standard} - A_{blank}} \times 100$$

The abbreviations have the following meanings:

A(standard or test substance):

Absorption of the wells with standard or test substance

A(zero standard):

Absorption of the wells without PGE$_2$ standard

A(blank):

Absorption of the wells without antibody, without peroxidase conjugate

A standard curve is generated by plotting the percent B/B0 as a function of the log PGE2 concentration. The PGE2 amount in the unknown samples is calculated by interpolating from the percent B/B0 values to PGE2 concentrations.

The inhibition of the biosynthesis of PGE2 in the presence of test substances is calculated according to the following equation:

$$\text{Inhibition of } PGE2\ [\%] = 100 - \left(\frac{PGE2_{test\ substance} - PGE2_{without\ cells}}{PGE2_{control} - PGE2_{without\ cells}} \times 100\right)$$

The abbreviations have the following meanings:

PGE2 test substance:

Amount of PGE2 of the wells with test substance and with cells

PGE2 control:

Amount of PGE2 of the wells without test substance, but with cells

PGE2 without cells

Amount of PGE2 of the wells without cells

The IC50 is calculated from the inhibition of PGE2 release [%] in a series of dilutions of tested samples. This is the concentrations at which the biosynthesis of PGE2 is inhibited 50%. The results are shown in Table 4.

TABLE 4

| PGE2 Inhibition (mean value of at least 2 independent tests) | |
| --- | --- |
| Test Substance | IC50 |
| Ginger extract BIO3040 | 0.00020% ± 0.00005% |

Example 5

ABTS-Assay

In Vitro

With the help of the ABTS-assay the anti-oxidative capacity of test substances was measured. 2,2'-azino bis-(3-ethylbenzothiazoline 6-sulfonic acid) (ABTS) was transformed by potassium persulfate into the blue-green radical cation ABTS•+. Through the addition of anti-oxidants (test substances) the radical cations were reduced and discoloration took place, which was determined photometrically at 734 nm.

$$\text{Inhibition [\%]} = 100 - \left(\frac{A \text{ test substance}}{A \text{ control}} \times 100\right)$$

The abbreviations have the following meanings:
A test substance:
Absorption of the wells with test substance
A control:
Absorption of the wells without test substance From the inhibition of the radical formation [%] in a series of dilutions of tested samples the IC50 was calculated. This is the concentration at which the radical formation is inhibited by 50%. The results are shown in Table 5:

TABLE 5

| Activity based on the inhibition of radical formation (mean value from at least 2 independent tests) | |
| --- | --- |
| Test Substance | IC$_{50}$ (ppm) |
| Ginger extract BIO3040 | 12 |

Example 6

DCF Assay

In Vitro

Primary human dermal fibroblasts (Lonza) were seeded in a 96-well microtiter plate at a concentration of $0.5 \times 10^4$ cells/well. Cultivation took place at 37° C. and 5% $CO_2$ in DMEM, enriched with 10% foetal calf serum. Confluence was supposed to be around 70% at the time, the incubation with the test substances began. Various concentrations of the test substances were applied to the cells in DMEM. After 24 h of incubation, 100 µL $H_2$DCF-DA-solution (10 µM) incl. DAPI (1:1000) was added to all samples (excluded the background-control) and incubated for one hour to deesterify the $H_2$DCF-DA by cellular esterases. The resulting $H_2$DCF was thereby trapped inside the cell. After the incubation, the cells were washed and the prooxidant challenge was set (1 mM, 1 h). The resulting fluorescence was read at λex 504 nm; λem 524 nm. An increased level of ROS (reactive oxygen species) led to an increased amount of fluorescence.

The inhibition of the oxidation in the presence of test substances was calculated according to the following equation:

$$\text{Inhibition of oxidation [\%]} = 100 - \left(\frac{RFU_{test\ substance} - RFU_{withoutcells}}{RFU_{control} - RFU_{withoutcells}} \times 100\right)$$

The abbreviations have the following meanings:
RFU test substance:
Relative fluorescence units of the wells with test substance and with cells
RFU control:
Relative fluorescence units of the wells without test substance, but with cells
RFU without cells:
Relative fluorescence units of the wells without test substance and without cells (blank)

The IC50 was calculated from the inhibition [%] in a series of dilutions of tested samples. This is the concentration at which the oxidation is 50% inhibited. The results are shown in Table 6:

TABLE 6

| Activity based on the inhibition of oxidation (mean value from at least 2 independent tests) | | |
| --- | --- | --- |
| Test Substance | Concentration [% b.w.] | Intracellular ROS reduction [%] |
| Ginger pungent $CO_2$ extract (50% pungent components) | 0.0005 | 60 |
| Ginger $CO_2$ extract (30% pungent components) | 0.0005 | 47 |
| Ginger Hexan/Isopropanol 8:2 extract | 0.0005 | 49 |
| Ginger ethanol/water 1:1 extract | 0.0005 | 32 |
| Ginger water extract | 0.0005 | 22 |

The ginger extract according to the present invention is the extract with the highest anti-oxidative capacity in DCF assay.

Example 7

Heme Oxygenase-1 Expression

In Vitro

NHDF (normal human dermal fibroblasts) cells were disseminated in a 6-well plate in a concentration of $2 \times 10^5$ cells/well (DMEM, 10% FCS). After cultivation in fully enriched medium (DMEM, 10% FCS) for 48 h at 37° C. and 5% CO2, the serum content was reduced to 0.1% to synchronize the cell cycle. Various concentrations of the test substances, the negative control (untreated cells) and tert.-butylhydrochinon as positive control, are added and incubated for a further 24 h. The maximum concentration of the test substances used corresponds to 0.2 times the value of the IC20 value of the cytotoxicity assay. After cell lysis, the protein amount was determined using the Biorad BCA assay. All samples were adjusted to the same protein level before application on a fast Criterion Gel (Biorad) to perform electrophoresis for 20 minutes at 300 V. Thereafter the proteins were transferred to a PVDF membrane on a semi-dry blotter (30 minutes, 25 V). The blotted membrane is blocked for 4 hours in a 5% milk powder solution in TBST at 4° C. After washing, the membrane is incubated with the first antibody solution HO-1 from abcam (1:500 in 1% milk powder in TBST) over night. After this, washing is repeated and the membrane has to be incubated for 1 h in the second antibody solution (goat anti mouse coupled to HRP; 1:800 in 1% milk powder). After washing, the membrane is exposed to chemiluminescence HRP-substrate solution for 5 minutes. The resulting band pattern is detected with a chemiluminescence sensitive camera system (Vilber Lou mat). The quantification was done by densitometry, using the Image J freeware software. The results are shown in Table 7:

TABLE 7

HO-1 up-regulation relative to control

| Test Substance | Concentration [% b.w.] | Up-regulation |
|---|---|---|
| Ginger extract BIO3040 | 0.0005% | 34-fold |

Example 8

Hyaluronic Acid Assay

In Vitro

NHDF (normal human dermal fibroblasts) cells were disseminated in a 96-well microtiter plate in a concentration of $2 \times 10^4$ cells/well (DMEM, 10% FCS). After cultivation in fully enriched medium (DMEM, 10% FCS) for 48 h at 37° C. and 5% CO2, the serum content was reduced to 0.1% to synchronize the cell cycle. Various concentrations of the test substances and TGF-beta1 as internal standard are added and incubated for a further 72 h. The maximum concentration of the test substances used corresponds to 0.2 times the value of the IC20 value of the cytotoxicity assay. Hyaluronic acid is quantified by a competitive ELISA (TE-COmedical TE1017).

The percent bound for each standard and unknown substance is calculated using the following equation:

$$HA\_[ng/ml] = \frac{A_{standard\ or\ test\ substance} - A_{blank}}{A_{zero\ standard} - A_{blank}}$$

The abbreviations have the following meanings:

A(standard or test substance):

Absorption of the wells with standard or test substance

A(zero standard):

Absorption of the wells without HA standard

A(blank):

Absorption of the wells without antibody, without peroxidase conjugate

A standard curve is generated by plotting the percent B/B0 as a function of the log HA concentration. The HA amount in the unknown samples is calculated by interpolating from the percent B/B0 values to PGE2 concentrations.

$$\text{Induction of } HA\ [\%] = \left( \frac{HA_{test\ substance} - HA_{without\ cells}}{HA_{control} - HA_{without\ cells}} \times 100 \right)$$

The abbreviations have the following meanings:

HA test substance:

Amount of HA of the wells with test substance and with cells

HA control:

Amount of HA of the wells without test substance, but with cells

HA without cells

Amount of HA of the wells without cells

The results are shown in Table 8:

TABLE 8

Hyaluronic acid stimulation relative to control

| Test Substance | Concentration [% b.w.] | Stimulation |
|---|---|---|
| Ginger extract BIO3040 | 0.0000175% | 67.3% |
| | 0.000035% | 34.4% |
| | 0.00007% | 21.3% |

Formulation Examples for Skin Care Products

9=Skin-lightening day care fluid O/W
10=Shaving Cream O/W
11=After shave hydro gel
12=After-Sun spray O/W
13=Sunscreen lotion (O/W), broad-band protection
14=W/O night cream
15=Barrier repair cream O/W
16=Calming Balm
17=Antiperspirant pump spray
18=Body Wash
19=Body Oil
20=Anti-Cellulite Balm In Examples the following two perfume oils PFO1 and PFO2 were each used as fragrance (DPG 0 dipropylene glycol).

TABLE I

Perfume oil PFO1 with rose smell

| Component/Name | Parts b.w. |
|---|---|
| Acetophenone, 10% in DPG | 10.00 |
| n-Undecanal | 5.00 |
| Aldehyde C14, so-called (peach aldehyde) | 15.00 |
| Allylamyl glycolate, 10% in DPG | 20.00 |
| Amyl salicylate | 25.00 |
| Benzyl acetate | 60.00 |
| Citronellol | 80.00 |
| d-Limonene | 50.00 |
| Decenol trans-9 | 15.00 |
| Dihydromyrcenol | 50.00 |
| Dimethylbenzylcarbinyl acetate | 30.00 |
| Diphenyloxide | 5.00 |
| Eucalyptol | 10.00 |
| Geraniol | 40.00 |
| Nerol | 20.00 |
| Geranium oil | 15.00 |
| Hexenol cis-3, 10% in DPG | 5.00 |
| Hexenyl salicylate cis-3 | 20.00 |
| Indole, 10% in DPG | 10.00 |
| Alpha-ionone | 15.00 |
| Beta-ionone | 5.00 |

TABLE I-continued

Perfume oil PFO1 with rose smell

| Component/Name | Parts b.w. |
|---|---|
| Lilial ® (2-methyl-3-(4-tert-butyl-phenyl)propanal) | 60.00 |
| Linalool | 40.00 |
| Methylphenyl acetate | 10.00 |
| Phenylethyl alcohol | 275.00 |
| Styrolyl acetate | 20.00 |
| Terpineol | 30.00 |
| Tetrahydrolinalool | 50.00 |
| Cinnamyl alcohol | 10.00 |
| Total: | 1,000.00 |

TABLE II

Perfume oil PFO1 with rose smell

| Component/Name | Parts b.w. |
|---|---|
| Benzyl acetate | 60.00 |
| Citronellyl acetate | 60.00 |
| Cyclamenaldehyde (2-methyl-3-(4-isopropylphenyl)propanal | 20.00 |
| Dipropylene glycol (DPG) | 60.00 |
| Ethyllinalool | 40.00 |
| Florol (2-isobutyl-4-methyltetrahydro-2H-pyran-4-ol) | 30.00 |
| Globanone ® [(E/Z)-8-cyclohexadecen-1-one] | 180.00 |
| Hedione ® (methyldihydrojasmonate) | 140.00 |
| Hexenyl salicylate, cis-3 | 10.00 |
| Vertocitral (2,4-dimethyl-3-cyclohexenecarboxaldehyde) | 5.00 |
| Hydratropaaldehyde, 10% in DPG | 5.00 |
| Isodamascone (1-(2,4,4-trimethyl-2-cyclohexen-1-yl)-2-buten-1-one, 10% in DPG | 5.00 |
| Isomuscone (cyclohexadecanone) | 40.00 |
| Jacinthaflor (2-methyl-4-phenyl-1,3-dioxolane) | 10.00 |
| Cis-jasmone, 10% in DPG | 20.00 |
| Linalool | 50.00 |
| Linalyl acetate | 30.00 |
| Methyl benzoate, 10% in DPG | 25.00 |
| para-Methyl cresol, 10% in DPG | 10.00 |
| Nerol | 20.00 |
| Phenylpropylaldehyde | 5.00 |
| 2-Phenylethyl alcohol | 82.00 |
| Tetrahydrogeraniol | 13.00 |
| 2,2-Dimethyl-3-cyclohexyl-1-propanol | 80.00 |
| Total: | 1,000.00 |

TABLE III

Skin care compositions

| Component/INCI | 9 | 10 | 11 | 12 | 13 | 14 | 15 | 16 | 17 | 18 | 19 | 20 |
|---|---|---|---|---|---|---|---|---|---|---|---|---|
| Ginger extract acc. Invention | 0.05 | 0.1 | 0.1 | 0.25 | 0.1 | 0.15 | 0.1 | 0.2 | 0.03 | 0.2 | 0.15 | 0.08 |
| Alpha-Bisabol | — | 0.4 | | | | | | | 0.1 | | | 0.1 |
| Dimethicone Abil 350 | 0.5 | | | | | | 0.5 | | 2.0 | | | 3.0 |
| Allantoin | | | 0.1 | | | | | 0.1 | | | | |
| Aloe Vera Gel Concentrate | | | 1.0 | | 3.0 | | | | | | | |
| Aluminium stearate Alugel 34 TH | | | | | | 1.0 | | | | | | |
| Beta-Arbutin | 1.0 | | | | | | | | | | | |
| Laureth-2 Arlypon F | | | | | | | | | | | | |
| Avocado oil | | | | 3.0 | | | | | | | 2.0 | |
| Caffeine pure | | | | | | | | | | | | 1.0 |
| Carbomer Carbopol ETD | 0.2 | | | 0.2 | | | | | | | | |
| Acrylates/C10-30 Alkyl Acrylate Crosspolamer Carbopol Ultrez 21 | | | 0.4 | | | | | 0.6 | | | | |
| Cetylhydroxyproline palmitamide CeramideBio | | | | | | | 0.5 | | | | | |
| Hydroxyethyl Palmityl Oxyhydroxypropyl Palmitamide Ceramide SL | | | | | | | | 0.1 | | | | |
| Citric Acid | | | | | | | | | | | 0.3 | 0.2 |
| Cocamide MEA Comperlan 100 | — | — | — | — | — | — | — | — | — | 0.5 | — | — |
| Tocopherol Covi-Ox T-70 | — | — | — | 0.1 | — | — | — | — | — | — | 0.2 | — |
| Cyclohexasiloxane, Cyclopentasiloxane | — | — | — | 2.0 | 2.0 | — | — | — | — | — | — | — |
| Panthenol | — | — | 0.5 | 1.0 | — | — | — | — | 1.0 | — | — | — |
| Glyceryl Stearate Citrate | — | — | — | — | — | — | 1.5 | — | — | — | — | — |
| Glyceryl Stearate | — | — | — | — | — | — | 2.0 | — | — | — | — | — |
| Acrylates/C10-30 Alkyl Acrylate Crosspolymer | — | — | 0.4 | — | — | — | 0.6 | — | — | — | — | — |

TABLE III-continued

Skin care compositions

| Component/INCI | 9 | 10 | 11 | 12 | 13 | 14 | 15 | 16 | 17 | 18 | 19 | 20 |
|---|---|---|---|---|---|---|---|---|---|---|---|---|
| Cetylhydroxypro-line Palmitamide | — | — | — | — | — | — | 0.5 | — | — | — | — | — |
| Hydroxyethyl Palmityl Oxyhydroxypropyl Palmitamide | — | — | — | — | — | 0.1 | — | — | — | — | — | — |
| Citric Acid | — | — | — | — | — | — | — | — | — | 0.3 | — | 0.2 |
| Cocamide MEA | — | — | — | — | — | — | — | — | — | 0.5 | — | — |
| Tocopherol | — | — | — | 0.1 | — | — | — | — | — | — | 0.2 | — |
| Cyclohexasiloxane, Cyclopentasiloxane | — | — | — | 2.0 | 2.0 | — | — | — | — | — | — | — |
| Panthenol | — | — | 0.5 | 0.1 | — | — | — | 1.0 | — | — | — | — |
| Glyceryl Stearate Citrate Dracorin CE | — | — | — | — | — | — | 1.5 | — | — | — | — | — |
| Glyceryl Stearate Dracorin GMS | — | — | — | — | — | — | — | 2.0 | — | — | — | — |
| Glyceryl Oleate Citrate, Caprylic/Capric Triglyceride Dracorin GOC | — | — | — | 2.0 | — | — | — | — | — | — | — | — |
| Phenoxyethanol, Methylparaben, Ethylparaben, Butylparaben, Propylparaben, Isobutylparaben Dragocid Liquid | 0.8 | — | — | — | 0.7 | 0.8 | 0.8 | — | — | — | — | 0.4 |
| Glycerin, Triticum Vulgare (Wheat) Gluten, Water (Aqua) Dragoderm | — | — | — | — | — | — | — | — | — | 1.0 | — | — |
| Polyglyceryl-3-Polyricinoleate, Sorbitanisostearate Dragonsan W/O Liquid | — | — | — | — | — | 1.0 | — | — | — | — | — | — |
| Sorbitan Isostearate, Hydrogenated Castor Oil, Ceresin, Beeswax Dragosan W/O P | — | — | — | — | — | 6.0 | — | — | — | — | — | — |
| Bisabolol | 0.2 | — | — | — | — | — | — | — | — | — | — | — |
| Ethylhexyl Ethylisononanoate Dragoxat 89 | — | — | — | — | — | — | 2.0 | — | — | — | 10.0 | — |
| Stearic Acid, Palmitic Acid Edenor L2 | — | 24.0 | — | — | — | — | — | — | — | — | — | — |
| Coconut-Palmkernel Oil Fatty Acid Edenor K 12-18 | — | 10.0 | — | — | — | — | — | — | — | — | — | — |
| Tetrasodium EDTA | — | 0.2 | — | — | — | — | — | — | — | — | — | — |
| Disodium EDTA | 0.1 | — | — | — | 0.1 | — | — | 0.1 | — | 0.1 | — | — |
| Potassium Cetyl Phosphate, Hydrogenated Palm Glycerides Emulsiphos | 1.5 | — | — | — | 1.5 | — | 2.0 | — | — | — | — | — |
| Ethanol | — | — | — | — | — | — | — | — | — | 1.0 | — | — |
| Water (Aqua), Propylene Glycol, Paullinia Cupana Seed Extract, Alcohol Extrapone Guarana | — | — | — | — | — | — | — | — | — | 1.0 | — | — |
| Propylene Glycol, Hamamelis Virginiana (Witch Hazel) Water, Water (Aqua), Hamamelis Virginiana (Witch Hazel) Extract Extrapone Witch Hazel | — | — | — | — | — | 1.0 | — | 0.2 | — | — | — | — |
| Glycerin, Water (Aqua), Rosmarinus officinalis (Rosemary) Leaf Extract Extrapone Rosemary GW | — | — | — | — | — | — | 0.5 | — | — | — | — | — |
| Water (Aqua), Propylene Glycol, Potassium Iodide, Fucus Vesiculosus Extract Extrapone Seaweed | — | — | — | — | — | — | — | — | — | — | — | 2.5 |
| Fragrance PFO I, II | 0.3 | 1.0 | 0.1 | 0.25 | 0.4 | 0.4 | 0.3 | 0.2 | 1.0 | 0.5 | 0.5 | 0.4 |
| Menthone Glycerin Acetal Frecolat MGA | — | 0.5 | — | — | — | — | — | — | — | — | — | — |

TABLE III-continued

Skin care compositions

| Component/INCI | 9 | 10 | 11 | 12 | 13 | 14 | 15 | 16 | 17 | 18 | 19 | 20 |
|---|---|---|---|---|---|---|---|---|---|---|---|---|
| Menthyl Lactate Frescolat ML | — | — | 0.3 | 0.5 | — | — | — | — | — | 3.0 | — | — |
| Sodium Laureth Sulfate Genapol LRO | — | — | — | — | — | — | — | — | — | 37.0 | — | — |
| Zinc Gluconate Givobio GZN | — | — | — | — | — | — | 0.5 | — | — | — | — | — |
| Glycerin | 3.5 | 2.3 | — | 4.7 | 4.7 | 2.0 | 3.0 | 1.7 | — | — | — | — |
| Pentylene Glycol | — | — | 5.0 | 5.0 | — | — | — | — | 3.0 | 5.0 | — | — |
| Water, Pentylene Glycol, Glycerin, Sodium Lactate, Lactic Acid, Serine, Urea, Sorbitol, Sodium Chloride, Allantoin Hydrolite-5 | — | — | — | — | — | — | 1.0 | — | 1.0 | — | — | — |
| Diisopropyl Adipate | 2.0 | — | — | — | — | — | — | — | — | — | — | — |
| Triisononanoin | — | — | — | — | — | — | 3.0 | 1.0 | — | — | 10.0 | — |
| Sorbitol | — | — | — | — | — | 2.0 | — | — | — | — | — | — |
| Xanthan Gum | 0.2 | — | — | — | 0.2 | — | — | — | — | — | — | — |
| Kojic Acid | 0.5 | — | — | — | — | — | — | — | — | — | — | — |
| Cetyl Alcohol | 1.5 | — | — | — | 1.0 | — | 2.0 | — | — | — | — | — |
| Cetearyl Alcohol | — | — | — | — | — | — | — | — | — | — | — | — |
| Aluminium Chlorohydrate | — | — | — | — | — | — | — | — | 16.0 | — | — | — |
| *Macadamia Ternifoia* Seed Oil | — | — | — | — | — | — | — | — | — | — | 0.5 | — |
| Magnesium Chloride | — | — | — | — | — | 0.7 | — | — | — | — | — | — |
| Polyquaternium-7 | — | — | — | — | — | — | — | — | — | 0.5 | — | — |
| Paraffinum Liquidum | — | — | — | — | — | — | — | — | — | — | 52.5 | — |
| Butyl Methoxy-dibenzoyl-methane Neo Heliopan 357 | 2.0 | — | — | — | 1.0 | — | — | — | — | — | — | — |
| Disodium Phenyl Dibenzimidazole Tetrasulfonate Neo Heliopan AP | — | — | — | — | 10.0 | — | — | — | — | — | — | — |
| Ethylhexyl Methoxy-cinnamate Neo Heliopan AV | 7.5 | — | — | — | 3.0 | — | — | — | — | — | — | — |
| Benzophenone-3 Neo Heliopan BB | 3.0 | — | — | — | — | — | — | — | — | — | — | — |
| Phenylbenzimidazole Sulfonic Acid Neo Heliopan Hydro | — | — | — | — | 6.7 | — | — | — | — | — | — | — |
| Homosalate Neo Heliopan HMS | 10.0 | — | — | — | — | — | — | — | — | — | — | — |
| 4-Methylbenzyl-idene Camphor Neo Heliopan MBC | — | — | — | — | 1.5 | — | — | — | — | — | — | — |
| Ethylhexyl Salicylate Neo Heliopan OS | 5.0 | — | — | — | 5.0 | — | — | — | — | — | — | — |
| Trideceth-9, PEG-5 Ethylhexanoate, Water Neo PLC Water Soluble | — | — | 1.0 | — | — | — | — | — | 2.0 | — | — | — |
| Caprylic/Capric Triglyceride | — | 3.0 | — | 5.0 | 2.0 | — | 10.0 | — | — | — | — | — |
| BHT | — | — | — | — | — | 0.1 | — | — | — | — | — | — |
| Diethylhexyl Syringylidene Malonate) Oxynex 204 | — | — | — | — | — | — | 0.5 | — | — | — | — | — |
| PEG-26 Jojoba Acid, PEG-26 Jojoba Alcohol Oxypon 328 | — | — | — | — | — | — | — | — | — | — | — | 1.0 |
| Cetearyl Ethylhexoate PCL Liquid | — | — | — | 4.0 | — | — | — | 3.0 | — | — | 21.0 | — |
| Stearyl Heptanoate, Stearyl Caprylate PCL Solid | — | — | — | 0.5 | — | — | — | 1.0 | — | — | — | — |
| Cetearyl Ethylhexanoate, Isopropyl Myristate PCL Liquid | — | — | — | — | — | 12.5 | — | — | — | — | — | — |
| Acrylates/C10-30 Alkyl Acrylate Crosspolymer Pemulen TR-2 | — | — | — | 0.25 | — | — | — | — | — | — | — | — |
| Shea Butter | — | — | — | — | — | — | — | — | — | — | 0.5 | — |
| Potassium Hydroxide | — | 11.0 | — | — | — | — | — | — | — | — | — | — |
| Potassium Sorbate | — | — | — | 0.1 | — | — | — | — | — | — | — | — |

TABLE III-continued

Skin care compositions

| Component/INCI | 9 | 10 | 11 | 12 | 13 | 14 | 15 | 16 | 17 | 18 | 19 | 20 |
|---|---|---|---|---|---|---|---|---|---|---|---|---|
| Propylene Glycol | — | — | — | 5.0 | — | — | — | — | 3.0 | — | — | 2.0 |
| Retinyl Palmitate | — | — | — | — | — | — | 0.2 | — | — | — | 0.05 | — |
| Polyacrylamide, C 13-14 Isoparaffin, Laureth-7 Sepigel 305 | — | — | — | — | — | — | — | — | — | — | — | 2.0 |
| Sodium Ascorbyl Phosphate | 1.0 | — | — | — | — | — | — | — | — | — | — | — |
| Sodium Benzoate | — | — | — | — | — | — | — | — | — | 0.5 | — | — |
| Sodium Chloride | — | — | — | — | — | — | — | — | — | 1.0 | — | — |
| Sodium Hydroxide | — | 1.0 | — | — | — | — | — | — | — | — | — | — |
| Sodium Hydroxide | 0.2 | — | 0.7 | — | — | — | 0.3 | 1.0 | — | — | — | — |
| PEG-40 Hydrogenated Castor Oil, Trideceth-9, Water (Aqua) | — | — | 1.5 | — | — | — | — | — | 3.0 | — | — | — |
| *Helianthus Annuus* (Sunflower) Seed Oil | — | — | — | — | — | 5.0 | — | — | — | — | — | — |
| *Prunus dulcis* | — | — | — | — | — | 5.0 | — | — | — | — | — | — |
| Hydroxymethoxyphenyl Propylmethylmethoxy-benzofuran Sym3D | — | — | — | — | — | 0.25 | — | — | — | — | — | — |
| Butylene Glycol, Pentylene Glycol, Hydroxyphenyl Propamidobenzoic Acid SymCalmin | — | — | — | 0.2 | — | — | — | 1.0 | — | — | — | — |
| Dimethyl Phenyl 2-Butanol SymDeo MPP | — | — | — | — | — | — | — | — | 0.5 | — | — | — |
| 1,2-Hexanediol, Caprylyl Glycerol Symdiol 68 | — | — | — | — | — | — | — | 1.0 | — | — | 1.0 | — |
| Trimethylcyclohexyl Butylcarbamate SymFit 1617 | — | — | — | — | — | — | — | — | — | — | — | 0.1 |
| Water (Aqua), Glycerin, Beta-Glucan SymGlucan | — | — | — | 1.0 | — | — | — | — | — | — | — | — |
| Benzylidene Dimethoxy-dimethylindanone SymHelios | — | — | — | — | 0.1 | — | — | — | — | — | — | — |
| Maltodextrin, *Rubus Fruticosus* (Blackberry) Leaf Extract SymMatrix | — | — | — | — | 0.2 | 1.0 | — | — | — | — | — | — |
| Trideceth-9, PEG-5 Isononanoate, Water SymMollient W/S | — | — | — | — | — | — | — | — | — | 1.0 | — | — |
| Glycerin, Water (Aqua), Myristoyl Pentapeptide-8 SymPeptie 222 | — | — | — | — | — | — | — | — | — | — | — | 5.0 |
| Bisabolol, *Zingiber Officinale* Root Extract SymRelief 100 | — | — | — | — | — | — | — | — | — | — | 0.1 | — |
| Bisabolol, Hydroxymethoxyphenyl Decanone SymRelief S | — | — | 0.1 | 0.1 | — | — | — | — | — | — | — | — |
| Hexyldecanol, Bisabolol, Cetylhydroxyproline Palmitamide, Stearic Acid, *Brassica Campestris* (Rapeseed) Sterols SymRepair | — | — | — | — | — | — | — | — | — | — | 1.0 | — |
| *Aloe Barbadensis* SymVital | — | — | — | 0.1 | — | — | — | — | — | — | — | 0.5 |
| Phenylethyl Resorcinol SymWhite 377 | 0.5 | — | — | — | — | — | — | — | — | — | — | — |
| Talcum | — | — | — | — | — | — | — | — | — | — | — | 3.0 |
| Phytosterols | — | — | — | — | — | — | 0.3 | — | — | — | — | — |
| Water | | | | | | Ad 100 | | | | | | |

Formulation Examples for Hair Care Products

21=Clear shampoo
22=Pearlized Conditioner Shampoo
23=Hair Conditioner, Leave on
24=Hair Conditioner, Rinse off
25=Hair Setting Gel
26=Pump Hair Spray with UV Protection
27=Hair Ends Fluid without Silicon Oil
28=Anti-Dandruff Hair Tonic
29=Aerosol Hair Spray

TABLE IV

| Component/INCI | 21 | 22 | 23 | 24 | 25 | 26 | 27 | 28 | 29 |
|---|---|---|---|---|---|---|---|---|---|
| *Zingiber Officinale* (Ginger) Root Extract | 0.2 | 0.5 | 0.1 | 0.2 | 0.05 | 0.05 | 0.1 | 0.1 | 0.05 |
| Water (Aqua), Butylene Glycol, Malic Acid, *Actinidia Chinensis* (Kiwi) Fruit Juice, *Citrus Aurantium Dulcis* (Orange) Juice, *Citrus Paradisi* (Grapefruit) Juice, *Pyrus Malus* (Apple) Juice, Trideceth-9, *Prunus Amygdalus Dulcis* (Sweet Almond) Seed Extract Actipone Alpha Pulp | — | — | — | 1.0 | — | — | — | — | — |
| Aminomethylpropanol | — | — | — | — | — | 0.7 | — | — | — |
| Propylene Glycol, PEG-55 Propylene Glycol Distearate Antil 141 Liquid | — | 1.0 | — | — | — | — | — | — | — |
| PEG-200 Hydrogenated Glyceryl Palmitate, PEG-7 Glyceryl Cocoate Antil 200 | 1.5 | — | — | — | — | — | — | — | — |
| Carbomer Carbopol ETD 2001 | — | — | — | — | 0.7 | — | — | — | — |
| Citric acid | — | — | — | — | — | — | 0.2 | — | — |
| Vincylcaprolactam/VP/Dimethylaminoethyl-methacrylate Copolymer Copolymer VC 713 | — | — | — | — | — | — | — | — | 3.8 |
| Climbazole Crinipan AD | — | — | — | — | — | — | — | 0.1 | — |
| Cetrimonium Chloride Dehyquart A CA | — | 1.0 | 4.0 | — | — | — | — | 0.1 | — |
| Cocoamidopropyl Betaine Dehyton K | 6.0 | 8.0 | — | — | — | — | — | — | — |
| Panthenol | — | 1.0 | 1.0 | — | — | — | 3.0 | 0.5 | — |
| Water (Aqua), Glycerin, *Avena Sativa* (Oat) Kernel Extract DragoCalm | 1.0 | — | — | — | — | — | — | — | — |
| Bisabolol Dragosantol | — | — | 0.1 | — | — | — | — | — | — |
| Glycerin, Triticum Vulgare (Wheat) Gluten, Water Dragoderm | 0.3 | 1.0 | 2.0 | 2.0 | — | — | — | — | — |
| Ethanol | — | — | — | — | 5.0 | 84.0 | 18.0 | 39.0 | 35.8 |
| Glycol Distearate, Laureth-4, Cocoamidopropyl Betaine Euperlan PK 4000 | — | 2.5 | — | — | — | — | — | — | — |
| Water (Aqua), Glycerin, Wine Extract, Alcohol Extrapone Champagne GW | — | — | 2.0 | — | — | — | — | — | — |
| Menthyl Lactate Frescolat ML | — | — | — | — | 0.8 | — | — | — | — |
| Menthyl Ethylamido Oxalate Frescolat X-Cool | — | — | — | — | — | — | — | 0.5 | — |
| Sodium Laureth Sulfate Generol LRO liquid | 35.0 | — | — | — | — | — | — | — | — |
| Glycerin | — | — | — | — | 10.0 | — | 8.0 | — | — |
| Cetyl Alcohol, Behentrimonium Chloride, Triticum Vulgare (Wheat) Bran Extract, Linoleic Acid | — | — | — | 3.7 | — | — | — | — | — |
| Water (Aqua), Pentylene Glycol, Glycerin, Fructose, Urea, Citric Acid, Sodium Hydroxide, Maltose, Sodium PCA, Sodium Chloride, Sodium Lactate, Trehalose, Allantoin, Sodium Hyaluronate, Hydroviton Plus 2290 | — | — | — | — | — | — | — | 1.0 | — |
| Cetearyl Octanoate | — | — | — | — | — | — | 0.2 | — | — |
| Cetearyl Alcohol Lanette O | — | — | 3.5 | — | — | — | — | — | — |
| PVP Luviskol K30 Powder | — | — | — | — | 3.0 | — | — | — | — |
| PVP/VA Copolymer Luviskol VA37 E | — | — | — | — | — | 3.0 | — | — | — |
| Polyquaterinium-7 Merquat 550 | 0.5 | 1.0 | — | — | — | — | — | — | — |
| C12-15 Pareth-12 Mulsifan RT 203/80 | — | — | — | — | 4.0 | — | — | — | — |

TABLE IV-continued

Hair care formulations

| Component/INCI | 21 | 22 | 23 | 24 | 25 | 26 | 27 | 28 | 29 |
|---|---|---|---|---|---|---|---|---|---|
| Hydroxyethylcellulose Notrosol 250HHR | — | — | — | — | — | — | 0.6 | — | — |
| Maltodextrin, *Aspalathus Linearis* Leaf Extract Neo Actipone | — | 0.1 | — | — | — | — | — | — | — |
| Benzophenone-3 Neo Heliopan BB | 0.3 | 0.2 | — | — | — | 0.2 | — | — | — |
| Phenylbenzimidazole Sulfonic Acid Neo Heliopan Hydro | — | — | — | — | — | 0.2 | — | — | — |
| Trideceth-9, PEG-5 Ethylhexanoate, Water Neo-PCL Water Soluble N | 1.0 | — | — | — | — | — | — | — | — |
| Tetrahydroxypropyl Ethylendiamine Neutrol TE | — | — | — | — | 1.4 | — | — | — | — |
| Cetearyl Erhylhexanoate PCL Liquid 100 | — | — | — | — | — | — | — | — | 0.2 |
| PEG-15 Cocopolyamine Polyquart H-81 | — | — | 3.0 | — | — | — | — | — | — |
| Propane Butane | — | — | — | — | — | — | — | — | 60.0 |
| Water (Aqua), Glycerin, PEG-40 Hydrogenated Castor Oil, *Rosa Damascena* Flower Oil | — | 0.5 | — | — | — | — | — | — | — |
| Cyclopentasiloxane, Cyclohexasiloxane Rose CL forte | — | — | — | — | — | 0.1 | — | — | — |
| Sodium Chloride | 0.8 | 0.5 | 2.0 | — | — | — | — | — | — |
| Sodium Hydroxide | 0.5 | 0.1 | — | 0.5 | — | — | — | — | — |
| PEG-40 Hydrogenated Castor Oil, Trideceth-9, Propylene Glycol, Water (Aqua) | — | — | — | — | — | — | 2.0 | 0.8 | — |
| Pentylene Glycol, Butylene Glycol, Hydroxyphenyl Propamidobenzoic Acid SymCalmin | — | — | — | — | — | — | — | 1.0 | — |
| 1,2 Hexanediol, Caprylylglycol Symdiol 68 | — | — | — | — | 1.0 | — | 0.5 | — | — |
| *Echinacea Purpurea* Extract Symfinity 1298 | 0.05 | — | — | — | — | — | — | — | — |
| Pentylene Glycol, *Isochrysis Galbana* Extract Sym Hair Force 1631 | — | 0.5 | — | — | — | — | — | 3.0 | — |
| Trideceth-9, PEG-5 Isononaoate, Water (Aqua) SymMollient W/S | — | 1.0 | — | — | — | — | — | — | — |
| Phenoxyethanol, Decylene Glycol, 1,2 Hexanediol SymOcide PS | 0.8 | — | 0.5 | — | 1.0 | — | 1.0 | — | — |
| Bisabolol, Hydroxymethoxyphenyl Decanone Sym Relief S | — | — | — | — | — | — | — | 0.05 | — |
| Hexyldecanol, Bisabolol, Cetylhydroxyproline Palmitamide, Stearic Acid, *Brassica Campestris* (Rapeseed) Sterols Sym Repair 100 | — | — | 0.5 | — | — | — | — | — | — |
| Fragrance | 0.3 | 0.3 | 0.3 | 0.2 | 0.05 | 0.2 | 0.5 | 0.1 | 0.2 |
| Pentylene Glcol, 4-t-Butylcyclohexanol SymSitive 1609 | — | — | — | — | — | — | — | 1.0 | — |
| Water (Aqua), Pentylene Glycol, Sodium Lauryl Sulfoacetate, Sodium Oleoyl Sarcosinate, Sodium Chloride, Disodium Sulfoacetate, Sodium Oleate, Sodium Sulfate SymSol PF-3 | — | — | — | — | 1.0 | — | — | — | — |
| Caprylyl Glycol, 1,2-Hexanediol, Methylbenzyl Alcohol SymTriol | — | 0.5 | — | — | — | — | — | — | — |
| Sodium Laureth Sulfate Texapon N70 | — | 10.0 | — | — | — | — | — | — | — |
| Wasser (Aqua) | | | | | Ad 100 | | | | |

The invention claimed is:

1. A composition comprising a ginger extract comprising
   (a) 25 to 30% b.w. [6]-gingerol;
   (b) 5 to 10% b.w. [8]-gingerol;
   (c) 5 to 10% b.w. [10]-gingerol;
   (d) 1.5 to 4% b.w. [6]-shogaol;
   (e) 0.3 to 1.3% b.w. [8]-shogaol;
   (f) 0.03 to 1% b.w. [10]-shogaol; and
   (g) 0.001 to 1% b.w. zingerone, wherein
   the content of gingerols sums up to 35 to 50% b.w.,
   the content of shogaols sums up to 1.5 to 6% b.w.,
   the total content of pungent components sums up to about 42 to about 50% b.w., and
   the content of essential oil is less than about 5% b.w.

2. The composition of claim 1, obtained by subjecting dried ginger leaves or roots to solvent extraction or supercritical extraction with carbon dioxide.

3. A composition according to claim 1, wherein the composition is a cosmetic composition.

4. A composition according to claim 1, wherein the composition is a pharmaceutical composition.

5. A composition according to claim 1, in a form for oral administration.

6. A composition according to claim 1, wherein the composition is a medicament for protecting stem cells.

7. A composition according to claim 1, wherein the composition is a medicament for inhibiting the cyclooxygenase-2 (COX-2) activity and prostaglandin E2 release.

8. A composition according to claim 1, wherein the ginger extract is a protection agent for stem cells.

9. A composition according to claim 1, wherein the ginger extract is an anti-oxidant agent.

10. A composition according to claim 1, wherein the ginger extract is an anti-inflammation agent.

11. A composition according to claim 1, wherein the ginger extract is an anti-aging agent for skin and hair.

12. The composition of claim 2, wherein the total content of pungent components sums up to about 42 to about 50% b.w. and the content of essential oil is less than about 5% b.w.

13. A process for obtaining the ginger extract of claim 1, wherein (a) ginger roots are frozen at about −10 to about −25° C.;

(b) the frozen roots are shredded, cut and dried at about 20 to about 50° C. for about 10 to about 30 hours;

(c) the dried roots are subjected to supercritical extraction with carbon dioxide at about 25 to about 90° C. and about 220 to about 370 bar for up to 10 hours; and (d) the extraction product obtained after about 3 hours is collected while the forerun taken from the first three hours is dismissed.

14. A therapeutical method for preserving stem cells by oral administration of a working amount of the ginger extract of claim 1 to an individual.

15. A non-therapeutical method for preserving stem cells by topical administration of a working amount of the extract of claim 1 to skin or hair of an individual.

* * * * *